(12) United States Patent
Munigeti et al.

(10) Patent No.: US 9,884,833 B2
(45) Date of Patent: Feb. 6, 2018

(54) CRYSTALLINE FORMS OF NEUROTROPHIN MIMETIC COMPOUNDS AND THEIR SALTS

(71) Applicant: Pharmatrophix, Inc., Menlo Park, CA (US)

(72) Inventors: Rajgopal Munigeti, Reminderville, OH (US); Frank M. Longo, Menlo Park, CA (US)

(73) Assignee: PharmatrophiX, Inc., Menlo Park, CA (US)

( * ) Notice: Subject to any disclaimer, the term of this patent is extended or adjusted under 35 U.S.C. 154(b) by 0 days.

(21) Appl. No.: 15/264,425

(22) Filed: Sep. 13, 2016

(65) Prior Publication Data

US 2017/0158653 A1    Jun. 8, 2017

Related U.S. Application Data

(63) Continuation of application No. 14/432,183, filed as application No. PCT/US2013/062025 on Sep. 26, 2013, now abandoned.

(60) Provisional application No. 61/785,469, filed on Mar. 14, 2013, provisional application No. 61/706,273, filed on Sep. 27, 2012.

(51) Int. Cl.
*A61K 31/435*    (2006.01)
*C07D 295/13*    (2006.01)

(52) U.S. Cl.
CPC ........ *C07D 295/13* (2013.01); *C07B 2200/13* (2013.01)

(58) Field of Classification Search
CPC .................................................. C07D 295/13
USPC ...................................................... 514/237.8
See application file for complete search history.

(56) References Cited

U.S. PATENT DOCUMENTS

| | | | |
|---|---|---|---|
| 7,723,328 B2 | 5/2010 | Longo et al. | |
| 8,916,556 B2 | 12/2014 | Longo et al. | |
| 9,271,986 B2 * | 3/2016 | Munigeti | A61K 31/535 |
| 9,464,066 B2 | 10/2016 | Damodara | |
| 2004/0248984 A1 | 12/2004 | Krieglstein et al. | |
| 2006/0246072 A1 | 11/2006 | Longo et al. | |
| 2010/0267727 A1 | 10/2010 | Longo et al. | |
| 2011/0003819 A1 | 1/2011 | Longo et al. | |
| 2011/0230479 A1 | 9/2011 | Longo et al. | |
| 2012/0322799 A1 | 12/2012 | Damodara | |
| 2013/0005731 A1 | 1/2013 | Munigeti et al. | |
| 2014/0100224 A1 | 4/2014 | Longo et al. | |
| 2015/0111903 A1 | 4/2015 | Longo et al. | |
| 2015/0259278 A1 | 9/2015 | Munigeti | |
| 2016/0176832 A1 | 6/2016 | Munigeti et al. | |
| 2016/0229823 A1 | 8/2016 | Gopal | |
| 2017/0157127 A1 | 6/2017 | Longo et al. | |

FOREIGN PATENT DOCUMENTS

| | | |
|---|---|---|
| CN | 102740856 A | 10/2012 |
| DE | 19939910 A1 | 3/2001 |
| JP | 42005231 B | 3/1967 |
| JP | H1081661 A | 3/1998 |
| JP | 2008536844 A | 9/2008 |
| WO | WO-9616980 A1 | 6/1996 |
| WO | WO-0037462 A1 | 6/2000 |
| WO | WO-0114320 A1 | 3/2001 |
| WO | WO-2006113097 A2 | 10/2006 |
| WO | WO-2010102212 A2 | 9/2010 |
| WO | WO-2011060262 A1 | 5/2011 |
| WO | WO-2011066544 A2 | 6/2011 |

OTHER PUBLICATIONS

Co-pending U.S. Appl. No. 12/718,675, filed Mar. 5, 2010.
Co-pending U.S. Appl. No. 15/687,311, filed Aug. 25,2017.
Gould et al: "Salt selection for basic drugs", International Journal of Pharmaceutics, Elsevier BV, NL, val. 33, No. 1-3, 1986, pp. 201-217, XP025813036, ISSN: 0378-5173, DOI: 10.1 016/0378-5173(86)90055-4 [retrieved on Nov. 1, 1986].
Guillory J Ked- Brittain H G: "Generation of Polymorphs, Hydrates, Solvates, and Amorphous Solids", Jan. 1, 1999 (Jan. 1, 1999 ), Polymorphism in Pharmaceutical Solids; [Drugs and the Pharmaceutical Sciences ; 95], Marcel Dekker Inc, New York* Basel, pp. I-11,183, XP002350313, ISBN: 978-0-8247-0237-3.
Hirayama, Noriaki (ed.) Yuuki kagoubutsu kessho sakusei hando bukku- genri to nouhau—(Handbook of production of crystals of organic compounds—principles and knowhow), Maruzen Publishing Co. Ltd, Jul. 25, 2008, p. 57-84.
Jain, A. et al.: "Estimation of Melting Points of Organic Compounds", Industrial & Engineering Chemistry Research., val. 43, No. 23, Nov. 1, 2004 (Nov. 1, 2004 ), pp. 7618-7621, XP055363537, US, ISSN: 0888-5885, DOI: 10.1021/ ie049378m.
Kawaguchi, Yoko, et al., Drug and crystal polymorphism. Journal Human environment engineering. 2002; 4(2): 310-17.
Kojima, Takashi. lyakuhin kaihatsu niokeru kesshosei sentaku no kouritsuka wo mezashite (Aiming at efficient selection of crystallinity in the development of pharmaceutical products). Journal of Pharmaceutical science and technology. Japan Sep. 1 2008; 68(5): p. 344-349.
Longo, et al. Neurotrophin Small Molecule Mimetics: Candidate Therapeutic Agents for Neurological Disorders. Current Medicinal Chemistry—Central Nervous System Agents, vol. 5, No. 1, Mar. 2005, pp. 29-41(13). DOI:10.2174/1568015053202769.
Longo, et al. Neuroprotective strategies in Alzheimer's disease. NeuroRx. Jan. 2004;1(1):117- 27. Review.
Longo, et al. Neurotrophin-based strategies for neuroprotection. J Alzheimers Dis. Dec. 2004;6(6 Suppl):S13-7.
Longo, et al. Small molecule modulation of p75 neurotrophin receptor functions. CNS Neurol Disord Drug Targets. Feb. 2008;7(1):63-70.

(Continued)

*Primary Examiner* — Nizal Chandrakumar
(74) *Attorney, Agent, or Firm* — Wilson Sonsini Goodrich & Rosati

(57) ABSTRACT

The present invention includes crystalline forms of 2-amino-3-methyl-N-(2-morpholinoethyl)-pentanamide disulfate and crystalline forms of 2-amino-3-methyl-N-(2-morpholinoethyl)-pentanamide monosulfate. Furthermore, the present invention provides compositions comprising the crystalline forms and therapeutic use of the crystalline forms. In one embodiment, the crystalline compound is (2S,3S)-2-amino-3-methyl-N-(2-morpholinoethyl)-pentanamide.

13 Claims, 27 Drawing Sheets

(56) References Cited

OTHER PUBLICATIONS

Longo, et al. Synthetic NGF peptide derivatives prevent neuronal death via a p75 receptor-dependent mechanism. J Neurosci Res. Apr. 1, 1997;48(1):1-17.

Longo, et al. The in vitro biological effect of nerve growth factor is inhibited by synthetic peptides. Cell Regul. Jan. 1990;1(2):189-95.

Massa, et al. Alzheimer's therapeutics: neurotrophin domain small molecule mimetics. J Mol Neurosci. 2003;20(3):323-6.

Massa, et al. Alzheimer's therapeutics: neurotrophin small molecule mimetics. J Mol Neurosci. Aug.-Oct. 2002;19(1-2):107-11.

Massa, et al. Small, nonpeptide p75NTR ligands induce survival signaling and inhibit proNGF-induced death. J Neurosci. May 17, 2006;26(20):5288-300.

Saragovi, et al. Small molecule and protein-based neurotrophic ligands: agonists and antagonists as therapeutic agents. Expert Opinion on Therapeutic Patents 9.6 (1999): 737-751. DOI:10.1517/13543776.9.6.737.

Singhal, et al. Drug polymorphism and dosage form design: a practical perspective. Adv Drug Deliv Rev. Feb. 23, 2004;56(3):335-47.

Dawson, T.M. and Dawson, V.L., Molecular pathways of neurodegeneration in Parkinson's disease. Science, 2003. vol. 302. pp. 819-822.

Freedman, et al., Treatment optimization in multiple sclerosis. The Canadian Journal of Neurological sciences, 2004. vol. 31. pp. 157-168.

Henze, et al., Screening of Beta-2 agonists and confirmation of fenoterol, orciprenaline, reproterol and terbutaline with gas chromatographymass spectrometry as tetrahydroisoquinoline derivatives. Journal of Chromatography B, 751 (2001) 93-105.

Holscher, et al., Development of Beta-Amyloid-Induced Neurodegeneration in Alzheimer's Disease and Novel Neuroprotective Strategies. Reviews in the Neurosciences, 2005, Freund & Pettman, U.K., vol. 16, pp. 181-212.

\* cited by examiner

CRYSTALLINE FORMS OF NEUROTROPHIN MIMETIC COMPOUNDS AND THEIR SALTS

CROSS-REFERENCE TO RELATED APPLICATIONS

The present application is a continuation of U.S. application Ser. No. 14/432,183, filed on Mar. 27, 2015, which is a National Stage Entry of PCT/US2013/062025, filed on Sep. 26, 2013, which claims priority to U.S. Provisional Application No. 61/706,273, filed on Sep. 27, 2012, and U.S. Provisional Application No. 61/785,469, filed on Mar. 14, 2013, each incorporated herein by reference in its entirety.

FIELD OF THE INVENTION

The present invention relates to crystalline forms of neurotrophin mimetic compounds and crystalline forms of the salts and/or solvates of neurotrophin mimetic compounds, processes of preparing the crystalline forms, and methods of using the same.

BACKGROUND OF THE INVENTION

Neurotrophins are polypeptides that play a role in the development, function, and/or survival of certain cells, including neurons, oligodendrocytes, Schwann cells, hair follicle cells, and other cells. The death or dysfunction of neurons and other cell types has been directly implicated in a number of neurodegenerative disorders. It has been suggested that alterations in neurotrophin localization, expression levels of neurotrophins, and/or expression levels of the receptors that bind neurotrophins are therefore linked to neuronal degeneration. Degeneration occurs in the neurodegenerative disorders Alzheimer's, Parkinson's and ALS, among others. Degeneration of oligodendrocytes can occur in central nervous system injury, multiple sclerosis, and other pathological states.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed β-hairpin loops, referred to as loops 1, 2, and 4 that exhibit relatively high degrees of amino acid conservation across the neurotrophin family.

Mature neurotrophins bind preferentially to the receptors Trk and p75$^{NTR}$ (p75 neurotrophin receptor, also called the Low Affinity Nerve Growth Factor Receptor or LNGFR) while pro-neurotrophins, which contain an N-terminal domain proteolytically removed in mature fowls, interact principally with p75$^{NTR}$ and through their N-terminal domains, with the sorting receptor sortilin (Fahnestock, M., et al. (2001) Mol Cell Neurosci 18, 210-220; Harrington, A. W. et al. (2004) Proc Natl Acad Sci USA 101, 6226-6230; Nykiaer. A. et al., (2004) Nature 427, 843-848). p75$^{NTR}$ interacts with Trks and modulates Trk signaling, but is also independently coupled to several signaling systems, including pro-survival signals, IRAK/TRAF6/NF.kappa.B, PI3/AKT, and pro-apoptotic signals, NRAGE/JNK (Mamidipudi, V., et al. (2002) J Biol Chem 277, 28010-28018; Roux, P. P., et al. (2001) J Biol Chem 276, 23097-23104; Salehi, A. H., et al. (2000) Neuron 27, 279-288).

When administered for therapeutic use, neurotrophins exhibit suboptimal pharmacological properties, including poor stability with low scrum half lives, likely poor oral bioavailability, and restricted central nervous system penetration (Podulso, J. F., Curran, G. L. (1996) Brain Res Mol Brain Res 36, 280-286; Saltzman, W. M., et al (1999) Pharm Res 16, 232-240; Partridge, W. M. (2002) Adv Exp Med Bio 513, 397-430). Additionally, the highly pleiotropic effects of neurotrophins achieved through action of the dual receptor signaling network increases the chances of adverse effects.

It has been suggested that the unliganded form of p75$^{NTR}$ is proapoptotic, and that homodimerization induced by neurotrophin binding eliminates the effect (Wang, J. J., et al (2000) J Neurosci Res 60, 587-593), consistent with studies showing no effects on survival of monomeric p75$^{NTR}$ ligands, including monovalent Fabs (Maliartchouk, S., et al (2000) J Biol Chem 275, 9946-9956) and monomeric cyclic peptides (Longo, F. M.,. (1997) J Neurosci Res 48, 1-17), while related bivalent forms in each study promote cell survival. However, these monomeric ligands may not engage the receptor in the same way as the natural ligands. Though active NGF is a homodimers containing 2 potential p75$^{NTR}$ binding sites, recent structural evidence suggests that it engages only one p75$^{NTR}$ molecule, disallowing the binding of another (He, X. L., (2004) Science 304, 870-875).

Unfortunately, technical and ethical considerations have thus far hampered the development of therapeutic agents based upon neurotrophins. For example, it is technically difficult to produce sufficient quantities of pure neurotrophins using recombinant DNA techniques. Additionally, although it is possible to utilize human fetal cells to produce neurotrophins, the ethical ramifications raised by the use of such cells (typically obtained from an aborted fetus) have all but prevented the utilization of this approach. Accordingly, there is an unmet need in the art for the development of small molecule agents with favorable drug-like features based upon neurotrophins, i.e., neurotrophin mimetics, that are capable of targeting specific neurotrophin receptors for use in the treatment of disorders or diseases. U.S. Patent Application Publication Nos. 2006/024072 and 2007/0060526 describe certain neurotrophin mimetics, and the contents of these two publications are herein incorporated by reference in their entirety for all purposes.

Those skilled in the pharmaceutical arts understand that crystallization of an active pharmaceutical ingredient offers the best method for controlling important physiochemical qualities, such as stability, solubility, bioavailability, particle size, bulk density, flow properties, polymorphic content, and other properties. Thus, there is a need for crystalline forms of neurotrophin mimetics and processes to produce such forms. These crystalline forms should be suitable for pharmaceutical use.

SUMMARY OF THE INVENTION

In one embodiment, the present invention provides a crystalline form of 2-amino-3-methyl-N-(2-morpholinoethyl)-pentanamide disulfate. In another embodiment, the present invention provides crystalline forms of 2-amino-3-methyl-N-(2-morpholinoethyl)-pentanamide monosulfate, such as Monosulfate-1 and Monosulfate-2.

In one embodiment, the present invention provides a composition comprising any of the crystalline forms of the present invention.

In one embodiment, the present invention provides a method of treating a disorder involving degeneration or dysfunction of cells expressing p75 comprising administering to a patient in need of such treatment a composition comprising a crystalline form of the present invention.

DETAILED DESCRIPTION OF THE INVENTION

Figure 1:
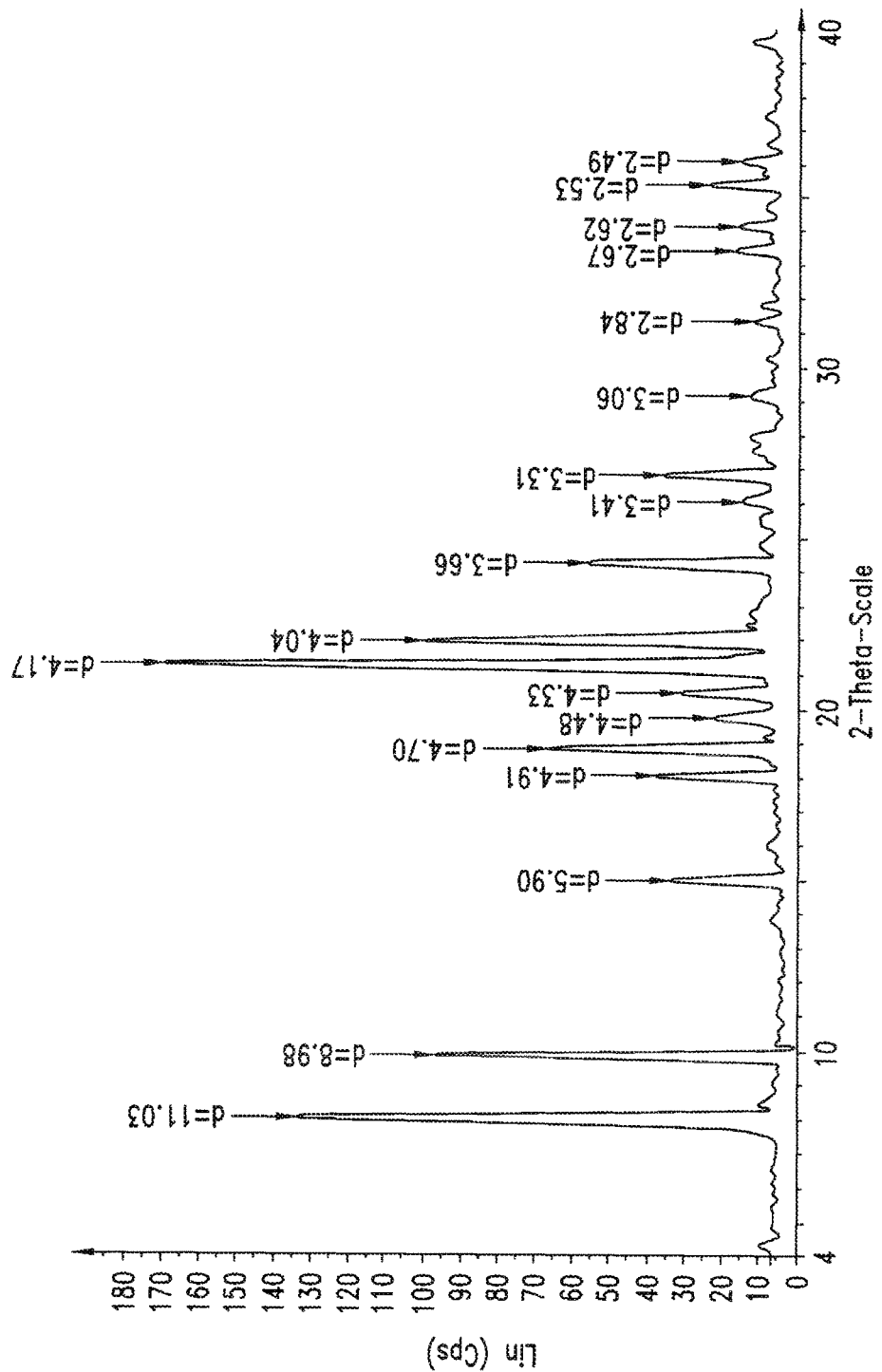
FIG. 1 is a graph of a x-ray powder diffraction (XRD) pattern of the crystalline disulfate salt of 2-amino-3-methyl-N-(2-morpholinoethyl)-pentanamide.

In patients with disorders related to degeneration or dysfunction of cells expressing p75, such as neurodegenerative disorders, alterations in neurotrophin localization, expression levels of neurotrophins, expression levels of the receptors that bind neurotrophins, and/or receptor signaling and functional outcomes can occur. Accordingly. by providing patients suffering from such disorders with a corresponding neurotrophic factor or mimetic thereof that modulates p75$^{NTR}$ function or proNGF/NGF binding to prevent cellular degeneration or dysfunction, such neural degeneration can be alleviated or prevented.

The present invention relates to crystalline forms of neurotrophin mimetic compounds as well as crystalline forms of salts and/or solvates of neurotrophin mimetic compounds. These crystalline materials can be formulated into pharmaceutical compositions and used for treating disorders involving degeneration or dysfunction of cells expressing p75.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the tei in "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

The term "compound(s) of the present invention", "present compound(s)", or "2-amino-3-methyl-N-(2-morpholinoethyl)-pentanamide" refers to the crystalline forms of 2-amino-3-methyl-N-(2-morpholinoethyi)-pentanamide salts and hydrates and/or solvates thereof described throughout the application, including a crystalline form of any single enantiomer of 2-amino-3-methyl-N-(2-morpholinoethyl)-pentanamide salts, hydrates and/or solvates thereof, a mixture of any two enantiomers of 2-amino-3-methyl-N-(2-morpholinoethyl)-pentanamide salts, hydrates and/or solvates thereof, a mixture of any three enantiomers of 2-amino-3-methyl-N-(2-morpholinoethyl)-pentanamide salts, hydrates and/or solvates thereof, and a mixture of any four enantiomers of 2-amino-3-methyl-N-(2-morpholinoethyl)-pentanamide salts, hydrates and/or solvates thereof.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

The term "composition" denotes one or more substances in a physical form, such as solid, liquid, gas, or a mixture thereof. One example of composition is a pharmaceutical composition, i.e., a composition related to, prepared for, or used in medical treatment.

The term "carboxylic acid" refers to an organic acid characterized by one or more carboxyl groups, such as acetic acid and oxalic acid. "Sulfonic acid" refers to an organic acid with the general formula of $R-S(O)_2-OH)_n$, wherein R is an organic moiety and n is an integer above zero, such as 1, 2, and 3. The term "polyhydroxy acid" refers to a carboxylic acid containing two or more hydroxyl groups. Examples of polyhydroxy acid include, but are not limited to, lactobionic acid, gluconic acid, and galactose.

"Neurotrophin mimetic compound" denotes an organic compound that resembles the biological function or activity of neurotrophin.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, omithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-cthylpiperidinc, benzylaminc, tetramethylammonium, tetracthylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethyl ammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A Gennaro, ed., 20th edition, Lippincott, Williams & Wilkins, Philadelphia, Pa.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein means an analytical spectrum, such as XRD pattern, $^1$H-NMR spectrum, FT-IR spectrum, Raman spectrum, TGA thermogram, etc., which resembles the reference spectrum to a great degree in both the peak locations and their intensity.

The terms "excipient", "carrier", and "vehicle" are used interexchangeably throughout this application and denote a substance with which a compound of the present invention is administered.

"Therapeutically effective amount" means the amount of a crystalline form that, when administered to a patient for treating a disease or other undesirable medical condition, is sufficient to have a beneficial effect with respect to that disease or condition. The therapeutically effective amount will vary depending on the crystalline form, the disease or condition and its severity, and the age, weight, etc. of the patient to be treated. Determining the therapeutically effective amount of a given crystalline form is within the ordinary skill of the art and requires no more than routine experimentation.

As used herein, the phrase "a disorder involving degeneration or dysfunction of cells expressing p75" includes, but is not limited to, disorders related to upregulation of p75. Such disorders include neurodegenerative disorders, as well as conditions involving degeneration of p75$^{NTR}$-expressing cells, such as hair loss, including chemotherapy-induced hair loss and age-related hair loss, and glaucoma. Within the nervous system, the p75 receptor is expressed by various cell types including neurons, oligodendrocytes, astrocytes. Compounds targeting p75 receptors expressed by neurons can be used to prevent loss of function, degeneration and/or death of neurons in a number of nervous system disorders including (but not limited to) Alzheimer's disease, Parkinson's disease, Huntington's disease, frontotemporal dementia, stroke, brain injury including traumatic brain injury, spinal cord injury, epilepsy, multiple sclerosis, dementia including HIV-induced dementia, cognitive impairment, anesthesia-induced cognitive impairment, amyotrophic lateral sclerosis and other motor neuron disorders, neuropathies including chemotherapy induced neuropathy and genetic neuropathies, myopathies, genetic, acquired or traumatic hearing loss, various forms of retinal degeneration including those associate with glaucoma, and Alzheimer's dementia associated with Down's Syndrome. In each of these disorders, neurons, oligodendrocytes, Schwann cells or other cells within the nervous system expressing p75 are affected.

In some embodiments, compounds targeting p75 receptors expressed by neurons can be used to treat disorders including age-related hair loss, chemotherapy-induced hair loss, Huntington's disease, Parkinson's disease, and frontotemporal dementia. In some embodiments, the compounds targeting p75 receptors expressed by neurons can be used to treat disorders including chemotherapy-induced neuropathy; HIV dementia; spinal cord injury; and Lewy body dementia.

Crystalline Materials

In one embodiment, the present invention provides a crystalline form of a salt and/or solvate of 2-amino-3-methyl-N-(2-morpholinoethyl)-pentanamide disulfate. In another embodiment, the present invention provides crystalline forms of a salt and/or solvate of 2-amino-3-methyl-N-(2-morpholinoethyl)-pentanamide monosulfate, such as Monosulfate-1 and Monosulfate-2. The compound of 2-amino-3-methyl-N-(2-morpholinoethyl)-pentanamide is selected from the group consisting of: (2S,3S)-2-amino-3-methyl-N-(2-morpholinoethyl)-pentanamide; (2R,3R)-2-amino-3-methyl-N-(2-morpholinoethyl)-pentanamide; (2R,3S)-2-amino-3-methyl-N-(2-morpholino-ethyl)-pentanamide; (2S,3R)-2-amino-3-methyl-N-(2-morpholinoethyl)-pentanamide; and mixtures thereof. Scheme A shows the chemical structures and absolute stereochemistry of the present compounds.

Scheme A:

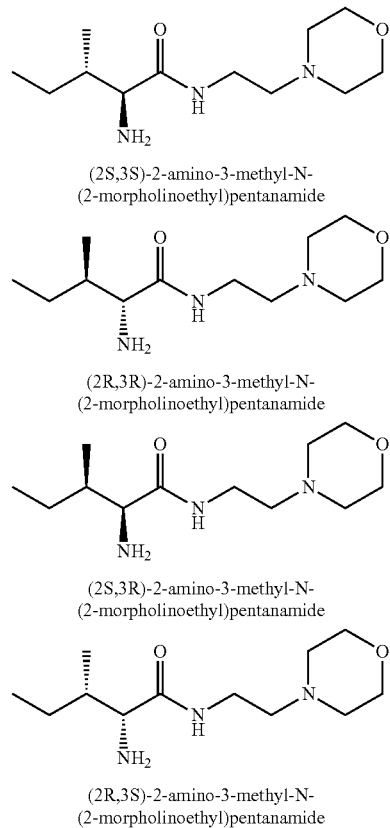

(2S,3S)-2-amino-3-methyl-N-(2-morpholinoethyl)pentanamide (2R,3R)-2-amino-3-methyl-N-(2-morpholinoethyl)pentanamide (2S,3R)-2-amino-3-methyl-N-(2-morpholinoethyl)pentanamide (2R,3S)-2-amino-3-methyl-N-(2-morpholinoethyl)pentanamide In one embodiment, the crystalline forms are characterized by the interlattice plane intervals determined by a X-ray powder diffraction pattern. The spectrum of XRD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRD can be selected according to the peak locations and their relative intensity to conveniently distinguish this crystalline structure from others.

Those skilled in the art recognize that the measurements of the XRD peak locations and/or intensity for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., about 9.016, to about 8.716−0.3, i.e., about 8.416. Depending on the sample preparation techniques, the calibration techniques applied to the instruments, human operational variation, and etc, those skilled in the art recognize that the appropriate error of margins for a XRD can be ±0.5; ±0.4; ±0.3; ±0.2; ±0.1; ±0.05; or less.

Additional details of the methods and equipments used for the XRD analysis are described in the Examples section.

In one embodiment, the crystalline form of 2-amino-3-methyl-N-(2-morpholinoethyl)-pentanamide disulfate exhibits an XRD comprising peaks at about 8.01, about 21.30 and about 21.99 degrees two-theta with the margin of error of about ±0.5; about ±0.4; about ±0.3; about ±0.2; about ±0.1; about ±0.05; or less. In another embodiment, the XRD of the crystalline form of 2-amino-3-methyl-N-(2-morpholinoethyl)-pentanamide disulfate further comprises peaks at about 9.85 and about 18.88 degrees two-theta with the margin of error of about ±0.5; about ±0.4; about ±0.3; about ±0.2; about ±0.1; about ±0.05; or less. In yet another embodiment, the crystalline form of 2-amino-3-methyl-N-(2-morpholinoethyl)-pentanamide disulfate exhibits an XRD comprising peaks shown in the table below:

TABLE 1

XRD Table of 2-amino-3-methyl-N-(2-morpholinoethyl)-pentanamide disulfate.

| Angle 2-Theta ° | d value Angstrom | Intensity % |
|---|---|---|
| 8.01 | 11.03 | 134 |
| 9.85 | 8.98 | 96.8 |
| 15.01 | 5.90 | 34.1 |
| 18.06 | 4.91 | 38.3 |
| 18.88 | 4.70 | 66.8 |
| 19.79 | 4.48 | 22.2 |
| 20.51 | 4.33 | 31.1 |
| 21.30 | 4.17 | 170 |
| 21.99 | 4.04 | 101 |
| 24.27 | 3.66 | 57.3 |
| 26.11 | 3.41 | 14.3 |
| 26.88 | 3.31 | 36.1 |
| 29.24 | 3.05 | 12.3 |
| 31.42 | 2.84 | 11.3 |
| 33.51 | 2.67 | 16.8 |
| 34.21 | 2.62 | 15.9 |
| 35.41 | 2.53 | 24.5 |
| 36.11 | 2.49 | 14.8 |

In one embodiment, the crystalline form of 2-amino-3-methyl-N-(2-morpholinoethyl)-pentanamide disulfate exhibits an XRD that is substantially similar to that shown in FIG. 1. In one embodiment, the compound 2-amino-3-methyl-N-(2-morpholinoethyl)-pentanamide disulfate as described in the above embodiments is (2S,3S)-2-amino-3-methyl-N-(2-morpholinoethyl)-pentanamide disulfate.

In another embodiment, the present invention provides a crystalline form of 2-amino-3-methyl-N-(2-morpholinoethyl)-pentanamide monosulfate ("Monosulfate-1") which exhibits an XRD comprising peaks at about 23.307, about 15.874 and about 7.896 degrees two-theta with the margin of error of about ±0.5; about ±0.4; about ±0.3; about ±0.2; about ±0.1; about ±0.05; or less. In another embodiment, the XRD of Monosulfate-1 further comprises peaks at about 21.018 and about 9.818 degrees two-theta with the margin of error of about ±0.5; about ±0.4; about ±0.3; about ±0.2; about ±0.1; about ±0.05; or less. In yet another embodiment, Monosulfate-1 exhibits an XRD comprising peaks shown in the table below:

TABLE 2

XRD Table of a crystalline form of 2-amino-3-methyl-N-(2-morpholinoethyl)-pentanamide monosulfate ("Monosulfate-1").

| Angle 2-Theta ° | d value Angstrom | Intensity Count |
|---|---|---|
| 27.632 | 3.22566 | 0.94 |
| 25.574 | 3.48034 | 0.67 |
| 25.016 | 3.55677 | 2.10 |
| 23.987 | 3.70695 | 1.11 |
| 23.307 | 3.81349 | 7.43 |
| 21.018 | 4.22340 | 2.27 |
| 19.401 | 4.57155 | 0.75 |
| 16.902 | 5.24129 | 1.21 |
| 15.874 | 5.57861 | 3.06 |
| 9.818 | 9.00151 | 2.91 |
| 7.896 | 11.18862 | 9.16 |

Figure 7:
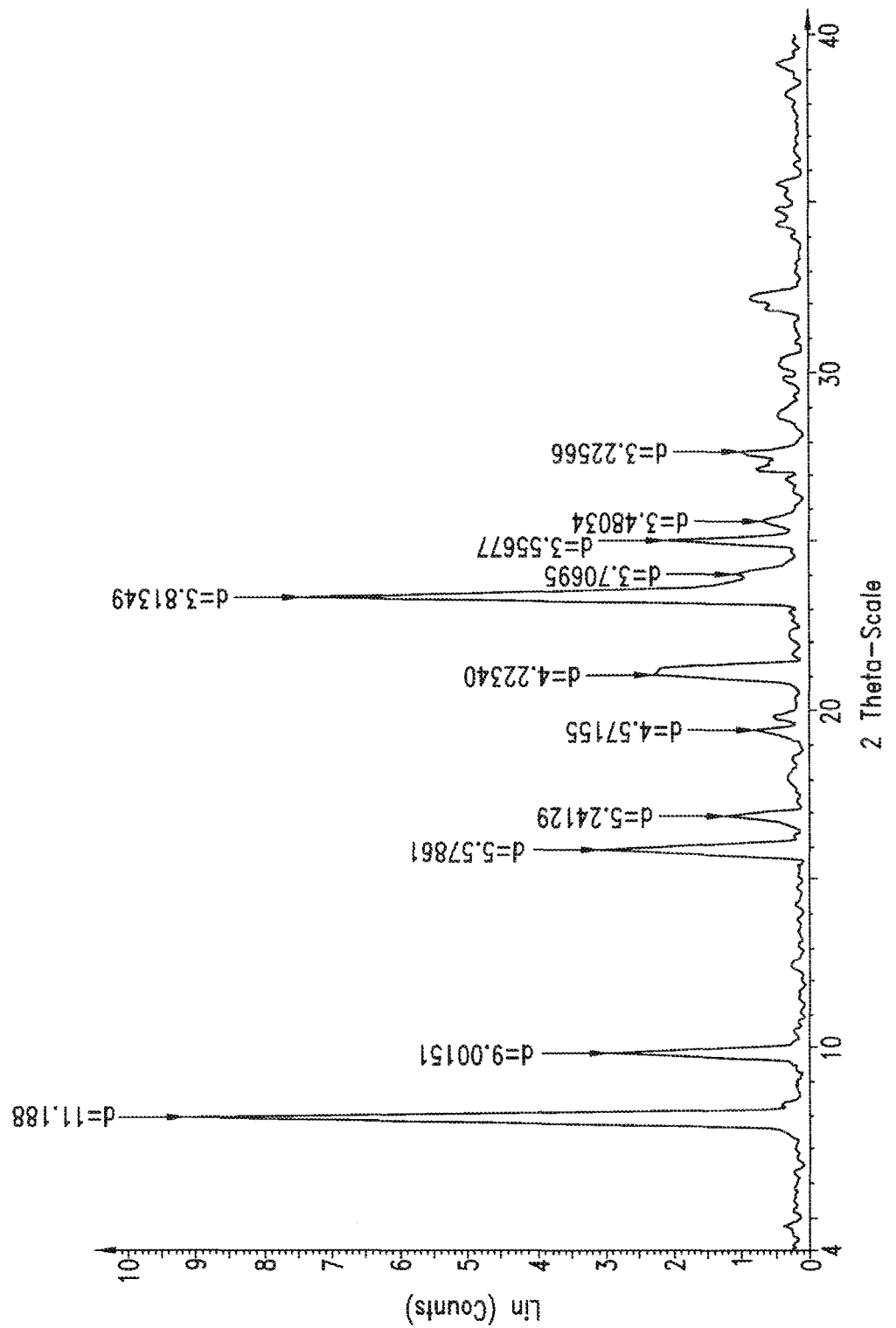
FIG. 7 is a graph of a XRD pattern of a crystalline monosulfate salt (Monosulfate-1) of 2-amino-3-methyl-N-(2-morpholinoethyl)-pentanamide.

In one embodiment, the crystalline form Monosulfate-1 of 2-amino-3-methyl-N-(2-morpholinoethyl)-pentanamide monosulfate exhibits an XRD that is substantially similar to that shown in FIG. 7. In one embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

In another embodiment, the present invention provides a crystalline form of 2-amino-3-methyl-N-(2-morpholinoethyl)-pentanamide monosulfate ("Monosulfate-2") which exhibits an XRD comprising peaks at about 7.92, about 17.97 and about 23.49 degrees two-theta with the margin of error of about ±0.5; about ±0.4; about ±0.3; about ±0.2; about ±0.1; about ±0.05; or less. In another embodiment, the XRD of the crystalline form of Monosulfate-2 further comprises peaks at about 9.83 and about 15.92 degrees two-theta with the margin of error of about ±0.5; about ±0.4; about ±0.3; about ±0.2; about ±0.1; about ±0.05; or less. In yet another embodiment, the crystalline form Monosulfate-2 of 2-amino-3-methyl-N-(2-morpholinoethyl)-pentanamide monosulfate exhibits an XRD comprising peaks shown in the table below:

TABLE 3

XRD Table of a crystalline form of 2-amino-3-methyl-N-(2-morpholinoethyl)-pentanamide monosulfate ("Monosulfate-2").

| Angle 2-Theta ° | d value Angstrom | Intensity Cps |
|---|---|---|
| 7.92 | 11.15 | 87.6 |
| 9.83 | 8.99 | 43.5 |
| 15.92 | 5.56 | 29.2 |
| 16.91 | 5.24 | 17.0 |
| 17.97 | 4.93 | 52.5 |
| 21.17 | 4.19 | 25.1 |
| 23.49 | 3.78 | 49.0 |
| 32.27 | 2.77 | 13.3 |

Figure 12:
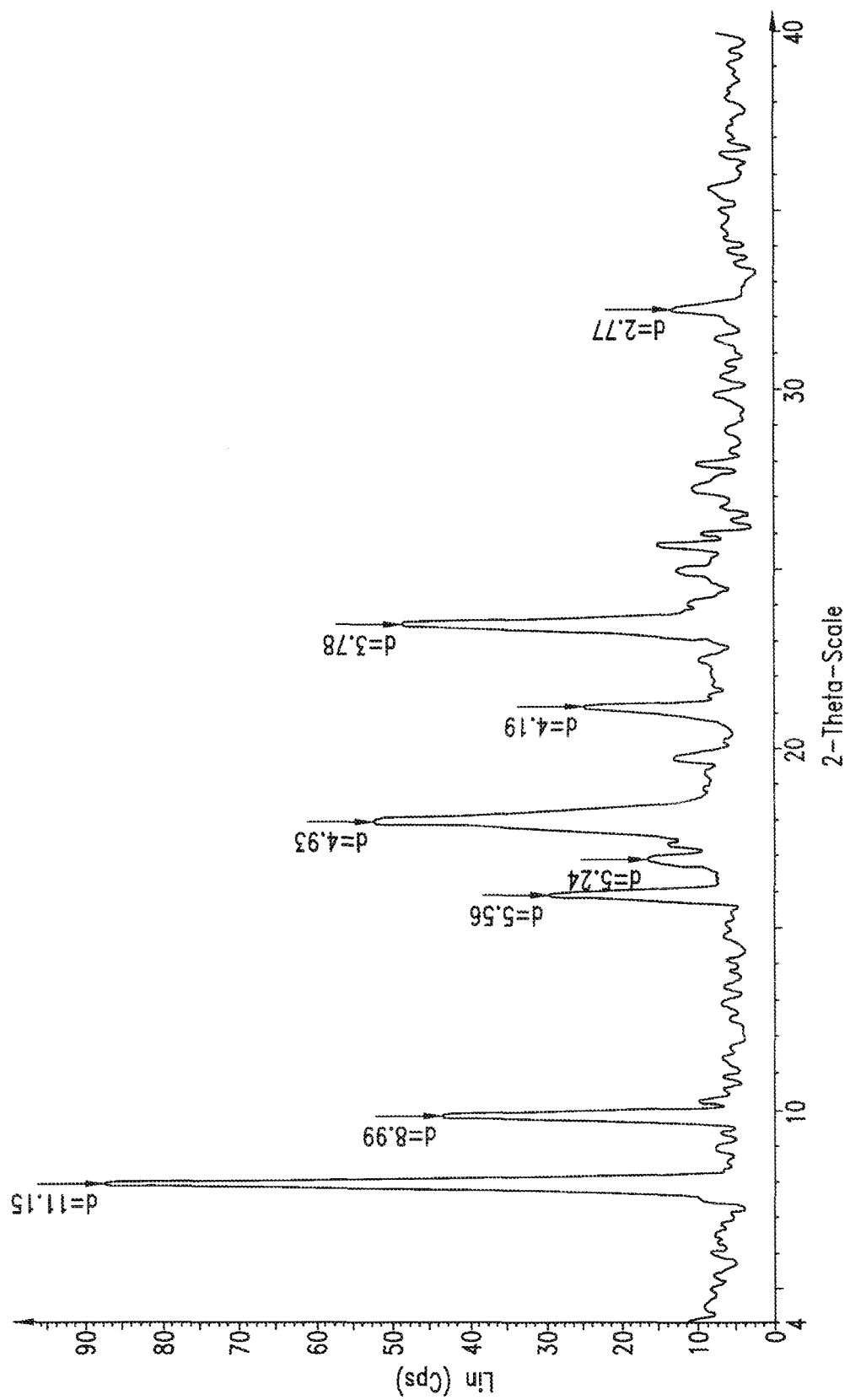
FIG. 12 is a graph of a XRD pattern of a crystalline monosulfate salt (Monosulfate-2) of 2-amino-3-methyl-N-(2-morpholinoethyl)-pentanamide.

In one embodiment, the crystalline form Monosulfate-2 of 2-amino-3-methyl-N-(2-morpholinoethyl)-pentanamide monosulfate exhibits an XRD that is substantially similar to that shown in FIG. 12. In one embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

In one embodiment, the crystalline forms are characterized by Raman spectroscopy. The Raman spectrum is typically represented by a diagram plotting the Raman intensity of the peaks versus the Raman shift of the peaks. The "peaks" of Raman spectroscopy are also known as "absorption bands". The intensities are often given in parenthesis with the following abbreviations: strong=st; medium=m; and weak=w. The characteristic peaks of a given Raman spectrum can be selected according to the peak locations and their relative intensity to conveniently distinguish this crystalline structure from others.

Those skilled in the art recognize that the measurements of the Raman peak shifts and/or intensity for a given crystalline form of the same compound will vary within a margin of error. The values of peak shift, expressed in reciprocal wave numbers ($cm^{-1}$), allow appropriate error margins. Typically, the error margins are represented by "±". For example, the Raman shift of about "1310±10" denotes a range from about 1310+10, i.e., about 1320, to about 1310−10, i.e., about 1300. Depending on the sample preparation techniques, the calibration techniques applied to the instruments, human operational variations, and etc, those skilled in the art recognize that the appropriate error of margins for a Raman shift can be ±12; ±10; ±8; ±5; ±3; ±1; or less.

Additional details of the methods and equipments used for the Raman spectroscopy analysis are described in the Examples section.

In one embodiment, the crystalline form of 2-amino-3-methyl-N-(2-morpholinoethyl)-pentanamide disulfate exhibits a Raman spectrum comprising peaks at about 1032.73 (s); about 976.30 (s); and about 851.86 (s) $cm^{-1}$ with the error of margin of about ±12; about ±10; about ±8; about ±5; about ±3; about ±1; or less. In another embodiment, the Raman spectrum further comprises peaks at about 1448.50 (m), about 1308.93 (m) and about 773.04 (m) $cm^{-1}$ with the error of margin of about ±12; about ±10; about ±8; about ±5; about ±3; about ±1; or less. In one specific embodiment, the crystalline form of 2-amino-3-methyl-N-(2-morpholinoethyl)-pentanamide disulfate exhibits a Raman spectrum that is substantially similar to FIG. 6. In another specific embodiment, the compound 2-amino-3-methyl-N-(2-morphol inoethyl)-pentanamide disulfate as described in the above embodiments is (2S,3S)-2-amino-3-methyl-N-(2-morpholinoethyl)-pentanamide disulfate.

In one embodiment, the crystalline form Monosulfate-1 of 2-amino-3-methyl-N-(2-morpholinoethyl)-pentanamide monosulfate exhibits an Raman spectrum comprising peaks at about 1451.20 (m); about 969.34 (s); and about 780.09 (m) $cm^{-1}$ with the error of margin of about ±12; about ±10; about ±8; about ±5; about ±3; about ±1; or less. In another embodiment, the Raman spectrum further comprises peaks at about 1308.71 (m), about 1021.17 (m) and about 493.04 (m) $cm^{-1}$ with the error of margin of about ±12; about ±10; about ±8; about ±5; about ±3; about ±1; or less. In one specific embodiment, the crystalline form of 2-amino-3-methyl-N-(2-morpholinoethyl)-pentanamide monosulfate exhibits a Raman spectrum that is substantially similar to FIG. 11. In another specific embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

In one embodiment, the crystalline forms are characterized by infrared (IR) spectroscopy. The IR spectrum is typically represented by a diagram plotting the intensity of the IR absorption peaks versus the wavenumber of the peaks. The intensities are often given in parenthesis with the following abbreviations: strong=st; medium=m; and weak=w. The characteristic peaks of a given IR spectrum can be selected according to the peak locations and their relative intensity to conveniently distinguish this crystalline structure from others.

Those skilled in the art recognize that the measurements of the IR peak shifts and/or intensity for a given crystalline form of the same compound will vary within a margin of error. The values of peak shift, expressed in reciprocal wave numbers ($cm^{-1}$), allow appropriate error margins. Typically, the error margins are represented by "±". For example, the IR shift of about "1310±10" denotes a range from about 1310+10, i.e., about 1320, to about 1310−10, i.e., about 1300. Depending on the sample preparation techniques, the calibration techniques applied to the instruments, human operational variations, and etc, those skilled in the art recognize that the appropriate error of margins for an IR shift can be ±12; ±10; ±8; ±5; ±3; ±1; or less.

In one embodiment, the crystalline form of 2-amino-3-methyl-N-(2-morpholinoethyl)-pentanamide disulfate exhibits an IR spectrum comprising peaks at about 2968 (s); about 1696 (s); and about 1175 (s) $cm^{-1}$ with the error of margin of about ±12; about ±10; about ±8; about ±5; about ±3; about ±1; or less. In another embodiment, the IR spectrum further comprises peaks at about 3322 (m), about 1023 (m) and about 855 (m) $cm^{-1}$ with the error of margin of about ±12; about ±10; about ±8; about ±5; about ±3; about ±1; or less. In one specific embodiment, the crystalline form of 2-amino-3-methyl-N-(2-morpholinoethyl)-pentanamide disulfate exhibits an IR spectrum that is substantially similar to FIG. 5. In another specific embodiment, the compound 2-amino-3-methyl-N-(2-morpholinoethyl)-pentanamide disulfate as described in the above embodiments is (2S,3S)-2-amino-3-methyl-N-(2-morpholinoethyl)-pentanamide disulfate.

In one embodiment, the crystalline form Monosulfate-1 of 2-amino-3-methyl-N-(2-morpholinoethyl)-pentanamide monosulfate exhibits an IR spectrum comprising peaks at about 2948 (s); about 1638 (s); and about 1097 (s) $cm^{-1}$ with the error of margin of about ±12; about ±10; about ±8; about ±5; about ±3; about ±1; or less. In another embodiment, the IR spectrum further comprises peaks at about 2589 (m), about 1079 (s) and about 613 (m) $cm^{-1}$ with the error of margin of about ±12; about ±10; about ±8; about ±5; about ±3; about ±1; or less. In one specific embodiment, the crystalline form of 2-amino-3-methyl-N-(2-morpholinoethyl)-pentanamide monosulfate exhibits a Raman spectrum that is substantially similar to FIG. 10. In another specific embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

Figure 14:
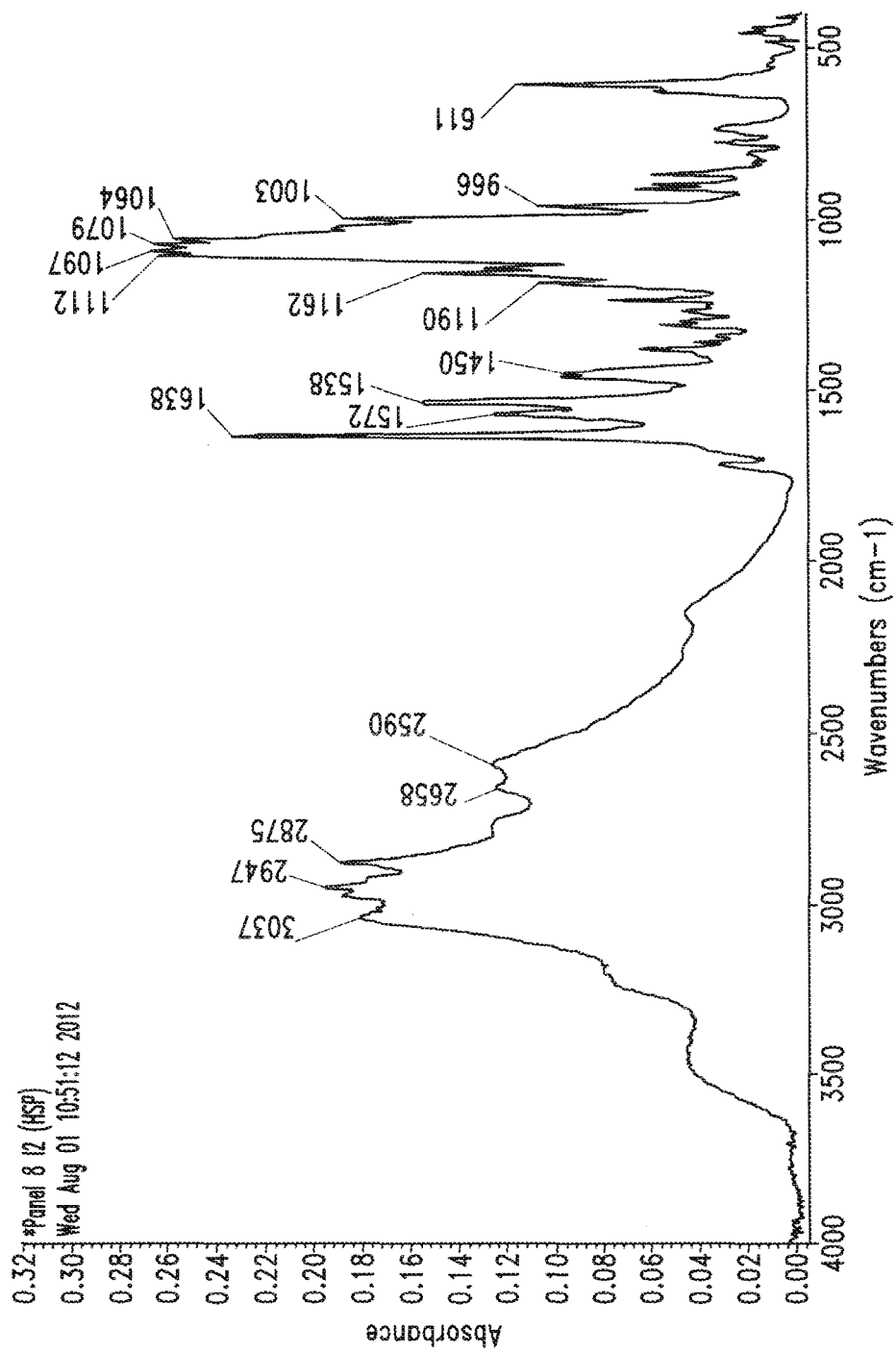
FIG. 14 is a graph of a FT-IR spectrum a crystalline monosulfate salt (Monosulfate-2) of 2-amino-3-methyl-N-(2-morpholinoethyl)-pentanamide.

In one embodiment, the crystalline form Monosulfate-2 of 2-amino-3-methyl-N-(2-morpholinoethyl)-pentanamide monosulfate exhibits an IR spectrum comprising peaks at about 2947 (s); about 1638 (s); and about 1097 (s) $cm^{-1}$ with the error of margin of about ±12; about ±10; about ±8; about ±5; about ±3; about ±1; or less. In another embodiment, the Raman spectrum further comprises peaks at about 3037 (s), 1538 (m) and about 1064 (s) cm$^{-1}$ with the error of margin of about ±12; about ±10; about ±8; about ±5; about ±3; about ±1; or less. In one specific embodiment, the crystalline form of 2-amino-3-methyl-N-(2-morpholinoethyl)-pentanamide monosulfate exhibits an IR spectrum that is substantially similar to FIG. 14. In another specific embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

In one embodiment, the crystalline forms are characterized by Differential Scanning Calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. The single maximum value of a DSV thennogram is often used as the characteristic peak to distinguish this crystalline structure from others.

Those skilled in the art recognize that the measurements of the DSC thermogram for a given crystalline form of the same compound will vary within a margin of error. The values of a single maximum value, expressed in degree C., allow appropriate error margins. Typically, the error margins are represented by "±". For example, the single maximum value of about "53.09±2.0" denotes a range from about 53.09+2, i.e., about 55.09, to about 53.09−2, i.e., about 51.09. Depending on the sample preparation techniques, the calibration techniques applied to the instruments, human operational variations, and etc, those skilled in the art recognize that the appropriate error of margins for a single maximum value can be ±2.5; ±2; ±1.5; ±1; ±0.5; or less.

Additional details of the methods and equipment used for the DSC thermogram analysis are described in the Examples section.

In one embodiment, the crystalline form of 2-amino-3-methyl-N-(2-morpholinoethyl)-pentanamide disulfate exhibits a DSC thermogram comprising an endotherm at about 216° C. with the error of margin of about ±2.5; about +2; about +1.5; about +1; about ±0.5; or less. In one specific embodiment, the crystalline form of 2-amino-3-methyl-N-(2-morpholinoethyl)-pentanamide disulfate exhibits a DSC thermogram that is substantially similar to FIG. 2A. In another specific embodiment, the compound 2-amino-3-methyl-N-(2-morpholinoethyl)-pentanamide disulfate as described in the above embodiments is (2S,3S)-2-amino-3-methyl-N-(2-morpholinoethyl)-pentanamide disulfate.

Figure 8A:
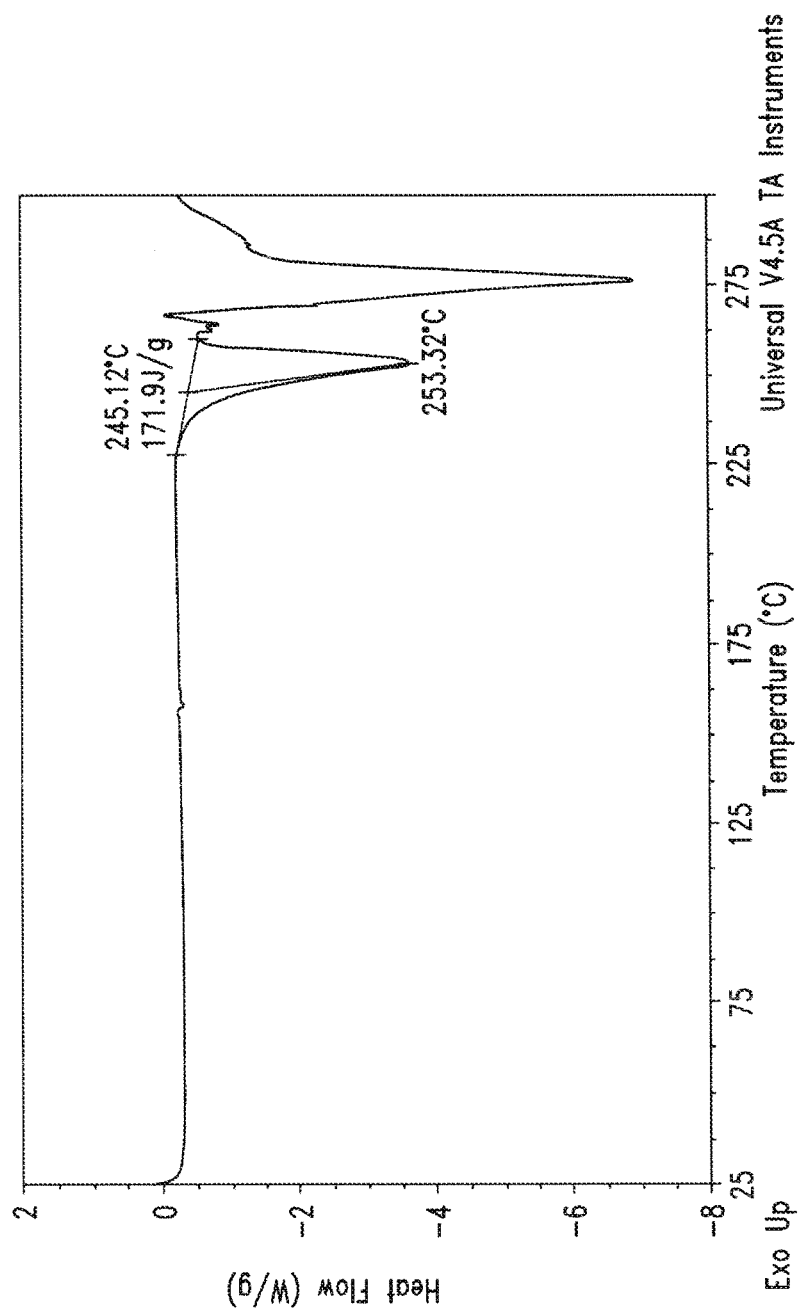
FIG. 8A is a DSC thermogram of a crystalline monosulfate salt (Monosulfate-1) of 2-amino-3-methyl-N-(2-morpholinoethyl)-pentanamide.

In one embodiment, the crystalline form Monosulfate-1 of 2-amino-3-methyl-N-(2-morpholinoethyl)-pentanamide monosulfate exhibits a DSC thermogram comprising an endotherm with an onset at about 245° C. with the error of margin of about ±2.5; about ±2; about ±1.5; about ±1; about ±0.5; or less. In one specific embodiment, the crystalline form of 2-amino-3-methyl-N-(2-morpholinoethyl)-pentanamide monosulfatc exhibits a DSC thermogram that is substantially similar to FIG. 8A. In another specific embodiment, the compound 2-amino-3-methyl-N-(2-morphol inoethyl)-pentanamide monosulfate as described in the above embodiments is (2S,3S)-2-amino-3-methyl-N-(2-morpholinoethyl)-pentanamide monosulfate.

In one embodiment, the crystalline form Monosulfate-2 of 2-amino-3-methyl-N-(2-morpholinoethyl)-pentanamide monosulfate exhibits a DSC thermogram comprising an endotherm with an onset at about 40° C. and an exotherm with an onset at about 99° C. with the error of margin of about ±2.5; about ±2; about ±1.5; about ±1; about ±0.5; or less. In one specific embodiment, the crystalline form of 2-amino-3-methyl-N-(2-morpholinoethyl)-pentanamide monosulfate exhibits a DSC thermogram that is substantially similar to FIG. 13. In another specific embodiment, the compound 2-amino-3-methyl-N-(2-morpholinoethyl)-pentanamide monosulfate as described in the above embodiments is (2S,3S)-2-amino-3-methyl-N-(2-morpholinoethyl)-pentanamide monosulfate.

Additional methods of characterize the present crystalline forms are described in the Example section of this application.

Pharmaceutical Formulations

In another embodiment, the present invention provides a pharmaceutical composition comprising a therapeutically effective amount of a crystalline form of the present invention as the active ingredient, combined with a pharmaceutically acceptable excipient or carrier. The excipients are added to the formulation for a variety of purposes.

Diluents may be added to the formulations of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

The present invention is not intended to encompass true solutions of 2-amino-3-methyl-N-(2-morpholinocthyl)-pentanamide monosulfatc, 2-amino-3-methyl-N-(2-morpholinocthyl)-pentanamide disulfate, or combination thereof whereupon the crystal structure of the novel crystalline forms and the properties that characterize the novel crystalline forms of 2-amino-3-methyl-N-(2-morpholinoethyl)-pentanamide monosulfate or 2-amino-3-methyl-N-(2-morpholinoethyl)-pentanamide disulfate of the present invention are lost. However, the use of the novel forms to prepare such solutions (e.g., so as to deliver 2-amino-3-methyl-N-(2-morpholinoethyl)-pentanamide monosulfatc, 2-amino-3-methyl-N-(2-morpholinoethyl)-pentanamide disulfate, or combination thereof in a liquid pharmaceutical formulation) is considered to be within the contemplation of the invention.

In liquid pharmaceutical compositions prepared using the crystalline forms of the present invention, 2-amino-3-methyl-N-(2-morpholinoethyl)-pentanamide monosulfate, 2-amino-3-methyl-N-(2-morpholinoethyl)-pentanamide disulfate, or combination thereof and any other solid excipients are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tctraacctic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The oral dosage form of the present invention is preferably in the form of an oral capsule or tablet having a dosage of about 5 mg to about 500 mg in total weight including the active ingredient and other excipients (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, or any other value or range of values therein), Daily dosages may include 1, 2, or more capsules per day.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tablcting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

It is not necessary that the formulations of the present invention contain only one crystalline form of atomoxetine hydrochloride. The crystalline forms of the present invention may be used in pharmaceutical formulations or compositions as single components or mixtures together with other crystalline forms of atomoxetine hydrochloride or with amorphous atomoxetine hydrochloride. However, it is preferred that the pharmaceutical formulations or compositions of the present invention contain 25-100% by weight, especially 50-100% by weight, of at least one of the novel forms, based on the total amount of atomoxetine hydrochloride in the formulation or composition. Preferably, such an amount of the novel crystalline form of atomoxetine hydrochloride is 75-100% by weight, especially 90-100% by weight. Highly preferred is an amount of 95-100% by weight.

Therapeutic Use

The present invention also provides treatment of disorders involving degradation or dysfunction of cells expressing p75.

In one aspect, there is provided a method for activating p75 receptors comprising contacting a cell containing a p75 receptor with the present crystalline form. Additionally disclosed are methods for treating nervous system disorders including (but not limited to) Alzheimer's disease, Parkinson's disease, Huntington's disease, stroke, traumatic brain injury, spinal cord injury, epilepsy, multiple sclerosis, amyotrophic lateral sclerosis, neuropathies, myopathies and various forms of retinal degeneration, based on the ability of the crystalline forms of the present invention to target p75 receptors expressed by neurons.

Additionally disclosed are methods for treating nervous system disorders including (and not limited to) multiple sclerosis, spinal cord injury and perinatal anoxia, based on the ability of the crystalline forms of the present application to target p75 receptors expressed by oligodendrocytes.

Further disclosed are methods for treating diseases other than those of the nervous system, particularly preventing loss of hair follicle cells and thereby preventing hair loss; preventing hepatic cirrhosis and promote liver regeneration; to regulate angiogenesis and promote neovascularization in the setting of diabetic wounds or other ischemic settings; to prevent cardiomyopathy by preventing myocardial cell loss or by stimulating growth of new cardiomyocytes either in the setting of ischemia or after myocardial infarction; and to inhibit tumor cell growth. In addition p75 is expressed by stem cells and is known to regulate stem cell growth; therefore, p75 ligands can be used to promote stem cell growth as part of a strategy to promote tissue and organ regeneration.

The present invention also provides methods of treating neurodegenerative and other disorders or conditions in a subject. More particularly, the methods of the present invention involve administration of a crystalline form in a subject to treat a neurodegenerative disorder or other disorder or condition. The crystalline form can be administered in an amount effective to induce survival signaling and/or inhibit proNGF-induced cell dysfunction, degeneration or death, which has been determined to be associated with neurodegenerative and other disorders. The terms "subject" and "patient" are used interchangeably throughout the present application.

The condition to be treated can be any condition which is mediated, at least in part, by binding of neurotrophins to $p75^{NTR}$. Such conditions include, but are not limited to, Alzheimer's disease, Huntington's disease, Pick's disease, amyotrophic lateral sclerosis, epilepsy, Parkinson's disease, spinal cord injury, stroke, hypoxia, ischemia, brain injury, traumatic brain injury, diabetic neuropathy, peripheral neuropathy, chemotherapy-induced neuropathy, nerve transplantation, multiple sclerosis, peripheral nerve injury, HIV related dementia, hair loss, chemotherapy-induced hair loss, age-related hair loss, glaucoma, retinal degeneration, cognitive impairment, anesthesia-induced cognitive impairment, disorders related to stem cell degeneration and disorders related to stem cell death.

The present crystalline form can be used to treat neural degeneration, including preventing neurodegeneration such as, for example, neurodegeneration caused by chemotherapy and/or neurodegenerative disorders, as well as other conditions such as inducing hair follicle cell survival caused by, for example, chemotherapy.

The present invention further provides for novel methods of facilitating cell survival. Representative cells include, but are not limited to, septal, hippocampal, cortical, sensory, sympathetic, motor neurons, hair follicle cells, progenitor, and stem cells. Generally, such cells include neurons, oligodendrocytes and hair follicle cells. Specifically, the methods comprise treating a cell with the present crystalline form, whereby the compound induces survival signaling and inhibits proNGF-induced cell death.

The present invention also discloses a method of administering the present crystalline form in order to ameliorate a condition mediated by $p75^{NTR}$ binding in a subject. The method can comprise the step of administering to a subject an effective amount of a crystalline form of the present invention.

As used herein, administering can be effected or performed using any of the various methods known to those skilled in the art. The crystalline form can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed crystalline forms can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the crystalline form is administered (e.g., syrup, elixir, capsule, tablet, foams, emulsion, gel, etc.) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The crystalline form can also be used to coat bioimplantable materials to enhance neurite outgrowth, neural survival, or cellular interaction with the implant surface. The crystalline forms and agents disclosed herein can be administered together with other biologically active agents, such as analgesics, anti-inflammatory agents, anesthetics and other agents which can control one or more symptoms or causes of a $p75^{NTR}$-mediated condition.

Additionally, administration can comprise administering to the subject a plurality of dosages over a suitable period of time. Such administration regimens can be determined according to routine methods, upon a review of the instant disclosure.

The crystalline forms of the present application can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases, including but not limited to amyloid-β inhibitors, acetylcholinesterase inhibitors, butyrylcholinesterase inhibitors, and N-methyl-D-aspartate subtype of glutamate receptor antagonists.

Crystalline forms of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. In some dosages, the crystalline forms disclosed herein are administered at about 5 mg/kg/dose. Time release preparations may be employed or the dose may be administered in as many divided doses as is convenient. When other methods are used (e.g. intravenous administration), crystalline forms are administered to the affected tissue at a rate from about 0.05 to about 10 mg/kg/hour, alternately from about 0.1 to about 1 mg/kg/hour. Such rates are easily maintained when these crystalline forms are intravenously administered as discussed herein. Generally, topically administered formulations are administered in a dose of about 0.5 mg/kg/dose to about 10 mg/kg/dose range. Alternately, topical foimulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg. Topical administration is appropriate for conditions such as hair loss or wound revascularization.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m².

Insofar as the crystalline forms disclosed herein can take the form of a mimetic or fragment thereof, it is to be appreciated that the potency, and therefore dosage of an effective amount can vary. However, one skilled in the art can readily assess the potency of a crystalline form of the type presently envisioned by the present application.

In settings of a gradually progressive nervous system disorder, crystalline forms of the present application are generally administered on an ongoing basis. In certain settings administration of a crystalline form disclosed herein can commence prior to the development of disease symptoms as part of a strategy to delay or prevent the disease. In other settings a crystalline form disclosed herein is administered after the onset of disease symptoms as part of a strategy to slow or reverse the disease process and/or part of a strategy to improve cellular function and reduce symptoms. Crystalline forms have been developed that cross the blood brain barrier and hence would be delivered by oral administration or by other peripheral routes. Crystalline forms that do not cross the blood brain barrier are applied for targets outside of the central nervous system. For targets and tissues outside of the nervous system, crystalline forms are applied in either acute or chronic settings by other oral or directed target administration such as by topical application.

It will be appreciated by one of skill in the art that dosage range will depend on the particular crystalline form, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific crystalline form employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when crystalline forms disclosed herein are used in accordance with the present application.

An effective amount of the crystalline forms disclosed herein comprise amounts sufficient to produce a measurable biological response. Actual dosage levels of active ingredients in a therapeutic crystalline form of the present application can be varied so as to administer an amount of the active crystalline form that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the present application, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the present application indicate effectiveness with respect to all vertebrate species which are to be included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the present application.

As such, the present application provides for the treatment of mammals such as humans, as well as those mammals of importance due to being endangered, such as Siberian tigers; of economic importance, such as animals raised on fauns for consumption by humans; and/or animals of social importance to humans, such as animals kept as pets or in zoos or farms. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

The following examples further illustrate the present invention but should not be construed as in any way limiting its scope.

EXAMPLES

Analytical Methods—various analytical methods, as described below, were applied to the present crystalline forms and their precursors to characterize their physiochemical properties.

Molecular Spectroscopy—$^1$H-NMR:

Samples were prepared by dissolving 1-10 mg in dimethylsulfoxide (DMSO)-$d_6$ with 0.05% (v/v) tetramethylsilane (TMS). Spectra were collected at ambient temperature on a Bruker Avance III 400 MHz FT-NMR spectrometer and Bruker Topspin software (version 2.1). Prior to each sample analysis, the magnetic field surrounding the sample was optimized by an automated shimming program.

Differential Scanning Calorimetry (DSC):

DSC data were collected on a TA Instruments Q2000 DSC. In general, samples in the mass range of 1 to 10 mg were crimped in aluminum sample pans and scanned from 25 to about 300° C. at 10° C./minute using a nitrogen purge of 100 mL/min.

Thermogravimetric Analysis (TGA):

TGA data were collected on a TA Instruments TGA Q500. In general, samples in the mass range of 1 to 15 mg were placed in an open, pre-tared platinum sample pan and scanned from 25 to about 300° C. at 10° C./minute using a nitrogen purge at 100 mL/min.

Infrared Spectroscopy:

Infrared spectra were obtained using a Nicolet 510 M-O Fourier transform infraredspectrometer, equipped with a Harrick Splitpea™ attenuated total reflectance device. Spectra were acquired from 4000 to 400 cm$^{-1}$ with a resolution of 4 cm$^{-1}$; 128 scans were collected for each analysis.

Raman Spectroscopy:

Raman spectra were obtained with a Thermo DXR dispersive Raman spectrometer using laser excitation at 780 nm. Spectra were acquired from 3300 to 300 cm$^{-1}$ (Raman shift) using a 400 line/mm wide-range dispersive grating and from 1850 to 300 cm$^{-1}$ (Raman shift) using an 830 line/mm high resolution dispersive grating. Each scan was nominally 10 sec, and 64 scans were collected for each analysis. Samples were analyzed as bulk powders.

X-Ray Powder Diffraction (XRD):

X-ray powder diffraction patterns were obtained using a Bruker D8 Discovery diffractometer equipped with an XYZ stage, laser video microscope for positioning, and a two dimensional HiStar area detector or scintillation detector. Collection times were nominally 3-30 mins. A Cu Kα radiation 1.5406 angstrom source operating at 40 kV and 40 mA was used to irradiate samples. The X-ray optics consists of a Gobel mirror coupled with a pinhole collimator of 0.5 mm. Theta-theta continuous scans were employed with a sample-detector distance of approximately 30 cm, which gives an effective 2θ range of 4-40°. Samples were mounted in low background quartz plates.

Hygroscopicity—Dynamic Vapor Sorption (DVS):

Samples were analyzed using an automated dynamic vapor sorption analyzer. The sample (about 1-10 mg) was dried in the instrument 0% RH for 6 hours. The samples were subjected to 0 to 95% RH back to 5% RH at 25° C. in 5% RH steps.

Water Content by Karl Fischer Analysis:

The apparent water content in samples was determined by Karl Fischer titration. The endpoint was detected by electrode when iodine is reduced by sulfur dioxide in the presence of water, an organic base, and a solvent (such as methanol). The test was performed either coulometrically or volumetrically. A Mitsubishi Moisturemeter, Model CA-100 was used for coulometric titration and a Brinkmann 716 DMS Titrino was used for the volumetric titration. Each sample was analyzed either in single replicate or duplicate based on sample availability.

Polymorph screening was performed on the disulfate salt of 2-amino-3-methyl-N-(2-morpholinoethyl)-pentanamide to determine the polymorphic behavior thereof, and identify polymorphs of the sulfate salts of 2-amino-3-methyl-N-(2-morpholinoethyl)-pentanamide. The screen was designed to discover as many crystalline forms as possible by using solvent recrystallization, anti-solvent addition, cooling crystallization, hydration experiments, and non-competitive slurry experiments.

Screening samples were characterized using differential scanning calorimetry (DSC), thermogravimetric analysis (TGA), Fourier transform nuclear magnetic resonance (NMR) spectroscopy, powder X-ray diffraction (XRD), dynamic vapor sorption desorption (DVS), Fourier transform infrared (FTIR) reflectance spectroscopy, and Raman spectroscopy. Sulfate analysis was also performed on various samples. Samples produced during the study exhibited three different crystalline arrangements, and one amorphous state. Detailed analysis of the crystalline arrangements revealed two monosulfate salts. The third observed crystalline arrangement was attributed to a stable and only observed polymorph of the disulfate salt form.

The test material used to screen for polymorphs was 2-amino-3-methyl-N-(2-morpholinoethyl)-pentanamide disulfate, which was used as supplied without further purification.

Figure 2A:
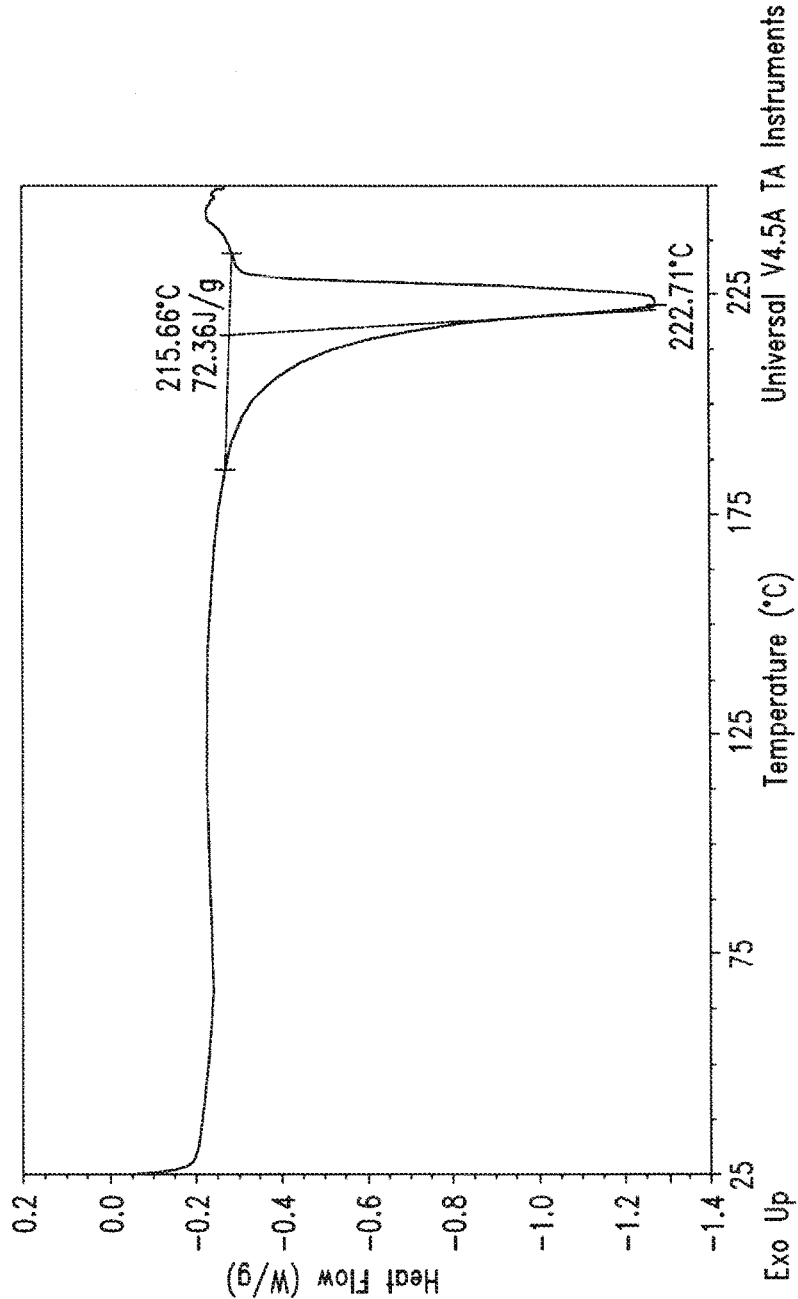
FIG. 2A is a differential scanning calorimetry (DSC) thermogram of the crystalline disulfate salt of 2-amino-3-methyl-N-(2-morpholinoethyl)-pentanamide.
Figure 2B:
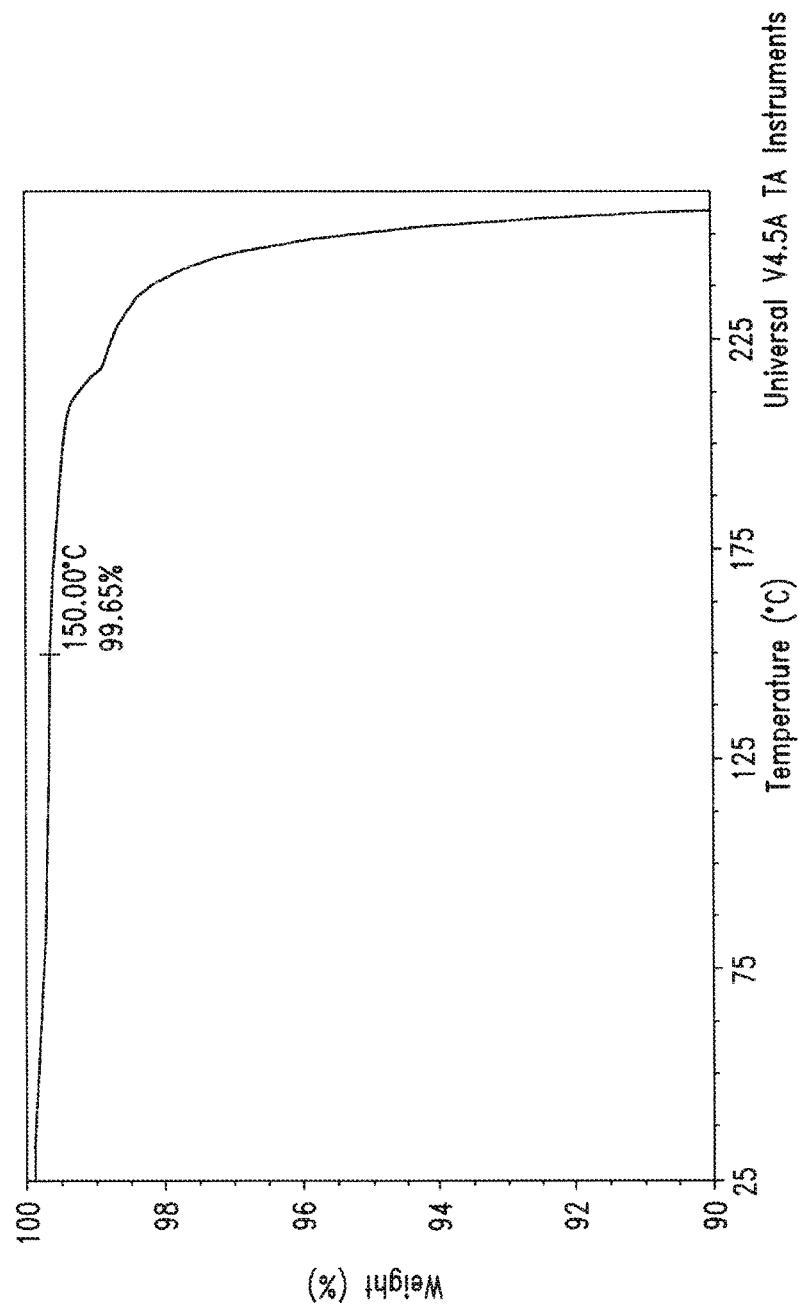
FIG. 2B is a thermogravimetric analysis (TGA) thermogram of the crystalline disulfate salt of 2-amino-3-methyl-N-(2-morpholinoethyl)-pentanamide.

Characterization of 2-amino-3-methyl-N-(2-morpholinoethyl)-Pentanamide Disulfate Starting Material:

X-ray powder diffraction was used to examine 2-amino-3-methyl-N-(2-morpholinoethyl)-pentanamide disulfate as supplied to determine if it was crystalline. FIG. 1 shows the XRD pattern of the supplied material. This form was crystalline and eventually designated as Form A. The thermal behavior of the supplied material was determined using differential scanning calorimetry and thermogravimetric analysis. The DSC thermogram of starting material did exhibit a single, well-defined melting endotherm with an extrapolated onset of 216° C., followed by decomposition. The TGA shows the supplied material (Form A) had less than 0.4% weight loss at 150° C., indicating the as received material is dry. FIGS. 2A and 2B show the DSC and TGA thermograms.

The water content of the as received material was determined by Karl Fischer to be approximately 0.3 wt %. The moisture sorption-desorption isotherms (FIGS. 3A and 3B) were collected using dynamic vapor sorption (DVS) analysis. This material did not sorb much water from 0% to 55%

RH under the experimental conditions, and then it shows rapid sorption up to 225 wt % water at 95% RH. In the desorption phase, the disulfate material shows a rapid desorption from 95% to 65% RH, then the sample desorbs at a relatively slow pace to a mass about 4 wt % greater than the original value at 0% RH. Apparent deliquescence at high humidity was followed by glass formation upon evaporation. A hydrate may also form near 60% RH.

Figure 4:
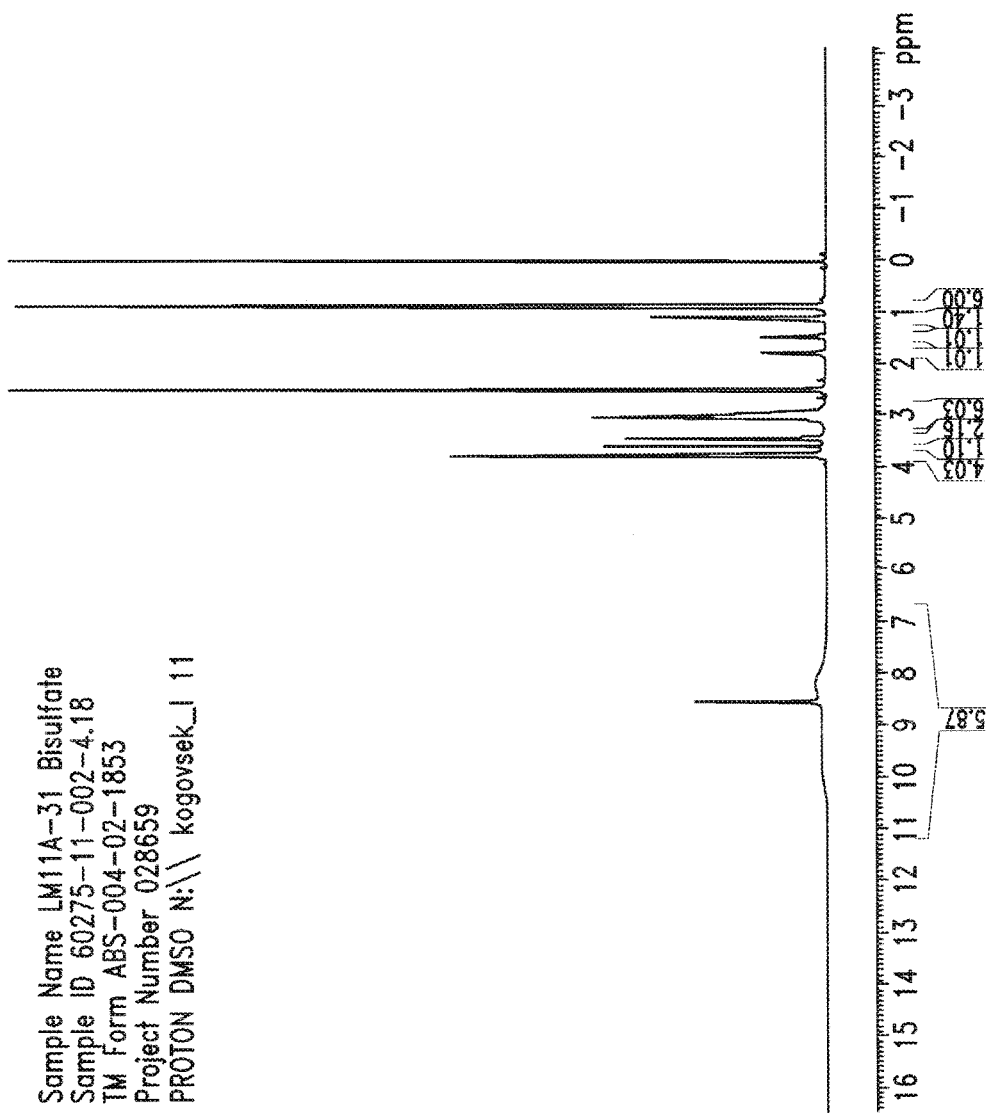
FIG. 4 is a $^1$H-NMR spectrum of the crystalline disulfate salt of 2-amino-3-methyl-N-(2-morpholinoethyl)-pentanamide.
Figure 5:
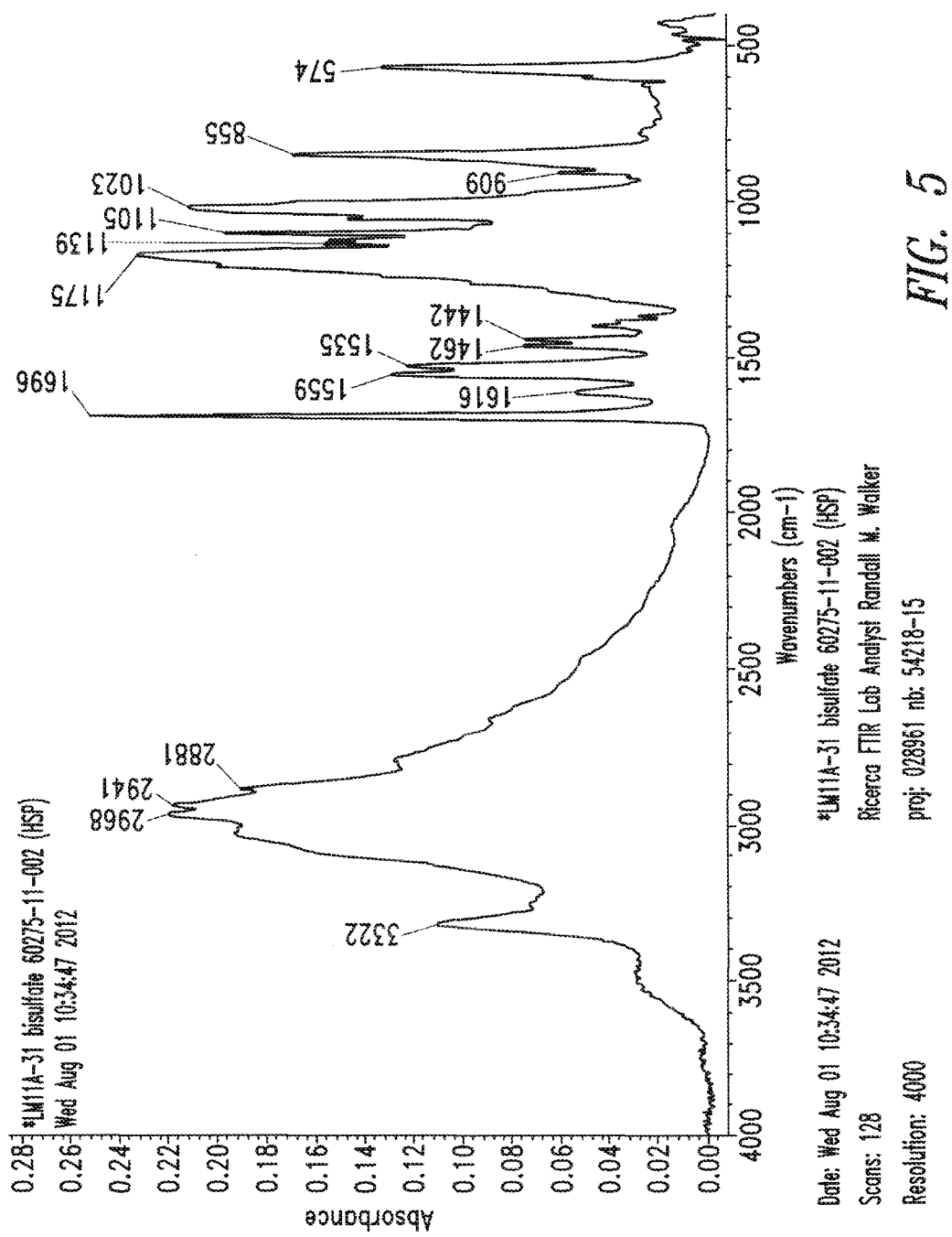
FIG. 5 is a graph of a FT-IR (Fourier transform infrared) spectrum the crystalline disulfate salt of 2-amino-3-methyl-N-(2-morpholinoethyl)-pentanamide.
Figure 6:
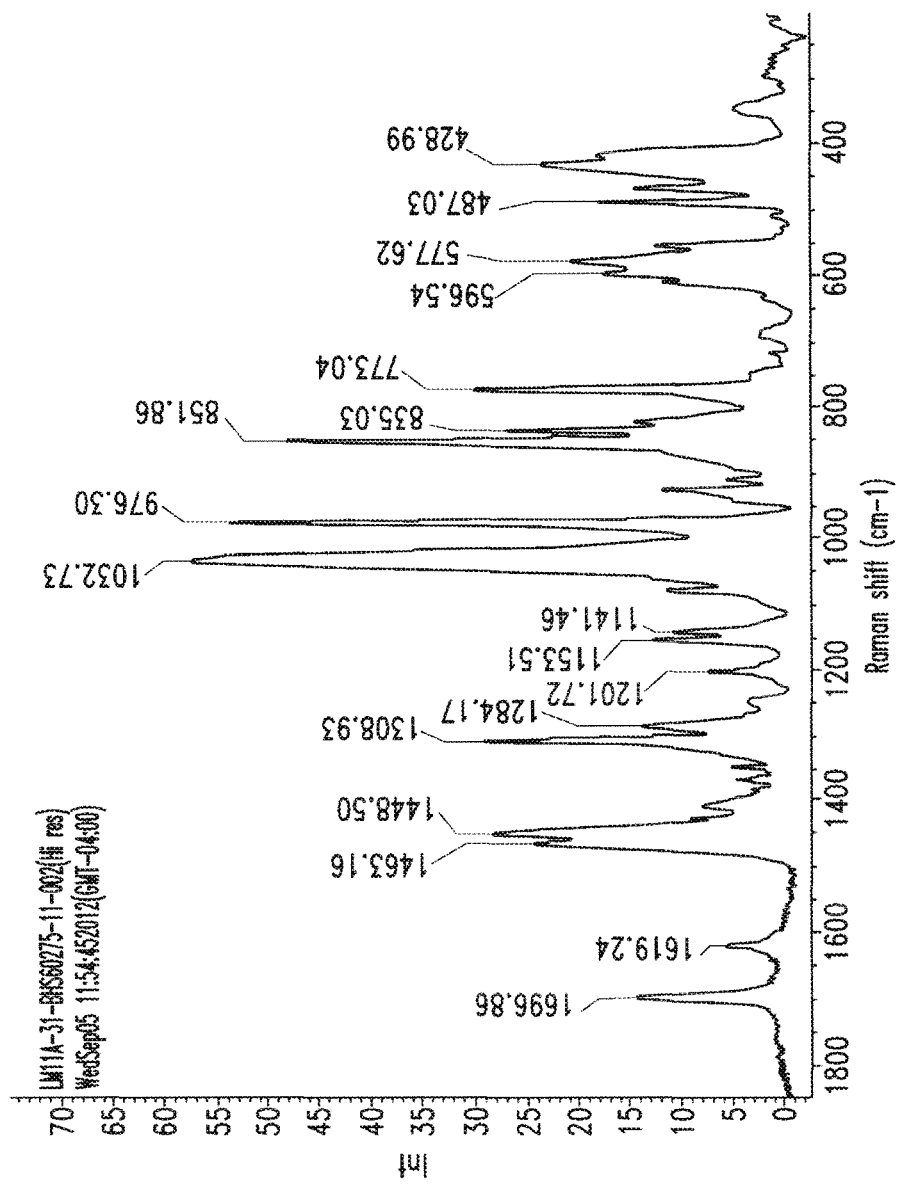
FIG. 6 is a graph of a Raman spectrum the crystalline disulfate salt of 2-amino-3-methyl-N-(2-morpholinoethyl)-pentanamide.

Proton NMR, FTIR and Raman spectra of this sample are given in FIGS. 4 through 6, respectively. The amount of sulfate in the 2-amino-3-methyl-N-(2-morpholinoethyl)-pentanamide disulfate material by ion chromatography (IC) was determined to be approximately 37 wt %.

Visual Solubility Measurement

About 100 mg of disulfate starting material was placed into each of 26 vials. Solvents were added and the vials were stirred for 30 minutes, followed by visual observation for remaining solids. Additional solvent was incrementally added until the solids were dissolved, or a maximum volume of solvent was added and the experiment was terminated. This solubility data was used in designing experiments, selecting the solvents, anti-solvents for crystallization and slurry experiments, sample consumption, etc. The visual solubility was determined and shown in Table 4, below.

TABLE 4

Visual Solubility of 2-amino-3-methyl-N-(2-morpho-linoethyl)-pentanamide disulfate in various solvents

| Well | Solvent | Approx. Solubility (mg/mL) |
|---|---|---|
| 1 | methanol | ≥100 |
| 2 | ethanol | ≥50 |
| 3 | trifluoroethanol | ≥50 |
| 4 | 1-propanol | ≤1.67 |
| 5 | 2-propanol | ≤1.67 |
| 6 | 1-butanol | ≤1.67 |
| 7 | 2-butanol | ≤1.67 |
| 8 | water | ≥100 |
| 9 | dimethylformamide (DMF) | ~1.67 |
| 10 | dimethylacetamide (DMA) | ≤1.67 |
| 11 | butylamine | ≤1.67 |
| 12 | diisopropylamine | ≤1.67 |
| 13 | pyridine | ≤1.67 |
| 14 | nitromethane | ≤1.67 |
| 15 | acetone | ≤1.67 |
| 16 | methyl ethyl ketone (MEK) | ≤1.67 |
| 17 | isopropyl ether | ≤1.67 |
| 18 | ethyl acetate (EtOAc) | ≤1.67 |
| 19 | methyl-t-butyl ether (MTBE) | ≤1.67 |
| 20 | isopropyl acetate | ≤1.67 |
| 21 | tetrahydrofuran (THF) | ≤1.67 |
| 22 | acetonitrile | ≤1.67 |
| 23 | dichloromethane | ≤1.67 |
| 24 | chloroform | ≤1.67 |
| 25 | toluene | ≤1.67 |
| 26 | heptane | ≤1.67 |

Solvent Recrystallization

To perform the solvent-based portion of the polymorph screen, the test material was recrystallized using various solvents under approximately 400 different crystal growth conditions. The scale of the recrystallization experiments was approximately 1 to 15 mL. A cooling crystallization panel (2-5 mL scale), an anti solvent addition panel (5-20 mL scale), two 96-well plates (1 mL scale) and 4 larger scale panels (10-15 mL) were prepared. The primary method of changing the crystal growth conditions was by using binary gradient arrays of solvent mixtures. The saturation temperature, growth temperature, and evaporation rate (relative supersaturation) were also varied to create additional differences in crystal growth conditions.

Saturated solutions were prepared by agitating excess (as possible) test material in contact with the various solvent systems at the saturation temperature. The mother liquor was separated from the residual solids by filtration if solids remained in the solution. The mother liquor was then heated above the saturation temperature (overheated) to dissolve any remaining solids. The temperature of each solution was then adjusted to the growth temperature and a controlled nitrogen shear flow was introduced to begin solvent evaporation.

The recrystallization conditions for the seven panels used during the study are summarized in Table 5 below.

TABLE 5

Summary of Recrystallization Panels for Solvent-Based Polymorph Screening

| Panel | No. of Wells | Scale (mL) | Solvent | Sat. Temp. (° C.) | Overheat Temp. (° C.) | Growth Temp. (° C.) | N₂ Flow (psi) |
|---|---|---|---|---|---|---|---|
| 1 | 26 | 15 | Single | 25 | 55 | ambient | 1.5 |
| 2 | 26 | 15 | Single | 25 | 65 | 40 | 1.5 |
| 3 | 30 | 15 | Binary | 40 | 50 | 40 | 1.5 |
| 4 | 8 | 5-15 | Anti-Solvent | n/a | n/a | 40 | 1.5 |
| 5 | 96 | 1 | Single/Binary | 25 | 55 | 40 | 2 |
| 6 | 45 | 15 | Binary | 25 | 40 | 35 | 1.5 |
| 7 | 96 | 1 | Binary | 25 | 35 | ambient | 0 |

Each recrystallization panel contained from 8 to 96 wells/tubes. The wells within each panel contained different solvent compositions. Because of the different solvent composition, each well acted as a different crystal growth experiment. The compositional solvent matrices for the recrystallization Panels used during the solvent-based portion of the polymorph screen are shown Tables 6 to 12, below.

TABLE 6

Recrystallization Panel 1

| Well | Solvent | XRD Form |
|---|---|---|
| 1 | methanol | n/a |
| 2 | ethanol | n/a |
| 3 | trifluoroethanol | glass |
| 4 | 1-propanol | n/a |
| 5 | 2-propanol | n/a |
| 6 | 1-butanol | n/a |
| 7 | 2-butanol | n/a |
| 8 | water | glass |
| 9 | dimethylformamide (DMF) | glass |
| 10 | dimethylacetamide (DMA) | glass |
| 11 | butylamine | gel |
| 12 | diisopropylamine | n/a |
| 13 | pyridine | gel |
| 14 | nitromethane | gel |
| 15 | acetone | n/a |
| 16 | methyl ethyl ketone (MEK) | n/a |
| 17 | isopropyl ether | n/a |
| 18 | ethyl acetate (EtOAc) | n/a |
| 19 | methyl-t-butyl ether (MTBE) | n/a |

TABLE 6-continued

Recrystallization Panel 1

| Well | Solvent | XRD Form |
|---|---|---|
| 20 | isopropyl acetate | n/a |
| 21 | tetrahydrofuran (THF) | n/a |
| 22 | acetonitrile | n/a |
| 23 | dichloromethane | n/a |
| 24 | chloroform | n/a |
| 25 | toluene | n/a |
| 26 | heptane | n/a |

TABLE 7

Recrystallization Panel 2

| Well | Solvent | XRD Form |
|---|---|---|
| 1 | methanol | n/a |
| 2 | ethanol | n/a |
| 3 | trifluoroethanol | n/a |
| 4 | 1-propanol | sticky-low yield |
| 5 | 2-propanol | sticky-low yield |
| 6 | 1-butanol | n/a |
| 7 | 2-butanol | n/a |
| 8 | water | n/a |
| 9 | dimethylformamide (DMF) | n/a |
| 10 | dimethylacetamide (DMA) | n/a |
| 11 | butylamine | n/a |
| 12 | diisopropylamine | n/a |
| 13 | pyridine | n/a |
| 14 | nitromethane | n/a |
| 15 | acetone | n/a |
| 16 | methyl ethyl ketone (MEK) | n/a |
| 17 | isopropyl ether | n/a |
| 18 | ethyl acetate (EtOAc) | n/a |
| 19 | methyl-t-butyl ether (MTBE) | n/a |
| 20 | isopropyl acetate | n/a |
| 21 | tetrahydrofuran (THF) | n/a |
| 22 | acetonitrile | n/a |
| 23 | dichloromethane | n/a |
| 24 | chloroform | n/a |
| 25 | toluene | n/a |
| 26 | heptane | n/a |

TABLE 8

Recrystallization Panel 5
Solvent Matrix and XRD Result for Recrystallization Panel 5

| Solvent | Sample ID | 1 | 2 | 3 | Co/AntiSolvent |
|---|---|---|---|---|---|
| | | Ratio of Solvents | | | |
| MeOH | A | 12:3 | 7.5:7.5 | 3:12 | Toluene |
| MeOH | B | 12:3 | 7.5:7.5 | 3:12 | DCM |
| Water | C | 12:3 | 7.5:7.5 | 3:12 | 1-propanol |
| Water | D | 12:3 | 7.5:7.5 | 3:12 | THF |
| DMF | E | 12:3 | 7.5:7.5 | 3:12 | THF |
| EtOH | F | 12:3 | 7.5:7.5 | 3:12 | ACN |
| 2-propanol | G | 12:3 | 7.5:7.5 | 3:12 | Chloroform |
| TFE | H | 12:3 | 7.5:7.5 | 3:12 | Heptane |
| EtOH | I | 12:3 | 7.5:7.5 | 3:12 | Nitromethane |
| EtOH | J | 12:3 | 7.5:7.5 | 3:12 | Ethyl acetate |
| | | XRD Form | | | |
| MeOH | A | NA | Form A | Form A | Toluene |
| MeOH | B | NA | NA | NA | DCM |
| Water | C | NA | NA | Form A | 1-propanol |
| Water | D | NA | NA | NA | THF |
| DMF | E | NA | NA | NA | THF |
| EtOH | F | Form A | Form A | Form A | ACN |
| 2-propanol | G | Form A | NA | New-2 | Chloroform |
| TFE | H | Form A | Form A | Form A | Heptane |
| EtOH | I | NA | Form A | Form A | Nitromethane |
| EtOH | J | NA | NA | NA | Ethyl acetate |

TABLE 9

Anti-solvent Addition Crystallization Panel 6.

| Well | Solvent | Anti-Solvent | XRD Form |
|---|---|---|---|
| 1 | Water | DMA | Form A |
| 2 | Water | 2-butanol | Form A |
| 3 | Water | MTBE | Form A |
| 4 | Water | MEK | NA |
| 5 | Water | ACN | NA |
| 6 | Water | Toluene | NA |
| 7 | Water | Pyridine | MS-1 |
| 8 | Water | Nitromethane | NA |

TABLE 10

Recrystallization Panel 7 (96 Well Plate, Columns 1 Through 5 in the Ratio of 50:50, 6 Through 8 in the Ratio of 25:75, 9 Through 12 in the Ratio of 75:25)

| | | 1-propanol 1 | IPA 2 | 1-butanol 3 | 2-butanol 4 | MEK 5 | Water 6 | DCM 7 | Heptane 8 | ACN 9 | Toluene 10 | CHCl3 11 | EtOAc 12 |
|---|---|---|---|---|---|---|---|---|---|---|---|---|---|
| A | Water | NP | NP | NP | NP | NP | NP | NP | NP | NP | NP | NP | NP |
| B | MeOH | NP | NP | NP | NP | NP | NP | NP | NP | NP | NP | NP | NP |
| C | DMA | NP | NP | NP | NP | NP | MS-1 | MS-1 | NP | NP | NP | NP | NP |
| D | EtOH | NP | NP | NP | NP | NP | NP | NP | NP | NP | NP | NP | NP |
| E | DMF | NP | NP | NP | MS-1 | NP | NP | MS-1 | NP | NP | NP | NP | NP |
| F | Pyridine | NP | NP | MS-1 | MS-1 | MS-1 | NP | NP | NP | NP | NP | NP | NP |
| G | Water | NP | NP | NP | NP | NP | NP | NP | NP | NP | NP | NP | NP |
| H | TFE | NP | NP | NP | NP | NP | NP | NP | NP | NP | NP | NP | NP |

NP = No Peaks (amorphous/no solids)

TABLE 11

Recrystallization Panel 8.
Solvent Matrix and XRD Result for Recrystallization Panel 8

| Solvent | Sample ID | 1 | 2 | 3 | Co/AntiSolvent |
|---|---|---|---|---|---|
| | | Ratio of Solvents | | | |
| MeOH | A | 10:5 | 7.5:7.5 | 5:10 | Nitromethane |
| MeOH | B | 10:5 | 7.5:7.5 | 5:10 | Ethyl acetate |
| TFE | C | 10:5 | 7.5:7.5 | 5:10 | Toluene |
| TFE | D | 10:5 | 7.5:7.5 | 5:10 | 2-propanol |
| TFE | E | 10:5 | 7.5:7.5 | 5:10 | 2-butanol |
| EtOH | F | 10:5 | 7.5:7.5 | 5:10 | Toluene |
| 2-propanol | G | 10:5 | 7.5:7.5 | 5:10 | Chloroform |
| DMF | H | 10:5 | 7.5:7.5 | 5:10 | Acetone |
| DMF | I | 10:5 | 7.5:7.5 | 5:10 | Heptane |
| DMF | J | 10:5 | 7.5:7.5 | 5:10 | 2-propanol |
| Water | K | 10:5 | 7.5:7.5 | 5:10 | Heptane |
| Water | L | 10:5 | 7.5:7.5 | 5:10 | Chloroform |
| Water | M | 10:5 | 7.5:7.5 | 5:10 | Nitormthane |
| Water | N | 10:5 | 7.5:7.5 | 5:10 | 2-butanol |
| Water | O | 10:5 | 7.5:7.5 | 5:10 | Dichloromethane |
| | | XRD Form | | | |
| MeOH | A | Form A | Form A | Form A | Nitromethane |
| MeOH | B | NA | Form A | Form A | Ethyl acetate |
| TFE | C | NA | Form A | Form A | Toluene |
| TFE | D | Form A | Form A | Form A | 2-propanol |
| TFE | E | Form A | Form A | Form A | 2-butanol |
| EtOH | F | Form A | NA | NA | Toluene |
| 2-propanol | G | Form A | Form A | MS-2 | Chloroform |
| DMF | H | Form A | Form A | NA | Acetone |
| DMF | I | Form A | MS-2 | NA | Heptane |
| DMF | J | Form A | Form A | NA | 2-propanol |
| Water | K | NA | Form A | Form A | Heptane |
| Water | L | Form A | NA | NA | Chloroform |
| Water | M | NA | NA | NA | Nitormthane |
| Water | N | NA | NA | NA | 2-butanol |
| Water | O | NA | NA | NA | Dichloromethane |

NA = No sample

TABLE 12

Recrystallization Panel 10 (96 Well Plate, Ratio of 50:50 in All the 96 Wells)

| | | IPA 1 | 2-butanol 2 | Nitro-methane 3 | Heptane 4 | 1-propanol 5 | Toluene 6 | 1-butanol 7 | MEK 8 | DCM 9 | CHCl3 10 | EtOAc 11 | ACN 12 |
|---|---|---|---|---|---|---|---|---|---|---|---|---|---|
| A | Water | NP | NP | MS-1 | NP | NP | NP | NP | NP | NP | NP | NP | NP |
| B | MeOH | NP | NP | NP | NP | NP | NP | NP | NP | NP | NP | NP | NP |
| C | DMA | NP | NP | NP | MS-1 | NP | NP | NP | NP | NP | MS-1 | NP | NP |
| D | EtOH | NP | NP | NP | NP | NP | NP | NP | NP | NP | NP | NP | NP |
| E | DMF | MS-1 | MS-1 | NP | NP | NP | MS-1 | NP | NP | NP | NP | NP | NP |
| F | Pyridine | NP | MS-1 | NP | NP | NP | NP | NP | NP | NP | MS-2 | NP | NP |
| G | Water | NP | NP | NP | NP | NP | NP | NP | NP | NP | NP | NP | NP |
| H | TFE | NP | NP | NP | NP | NP | NP | NP | NP | NP | NP | NP | NP |

MS-1 = Monosulfate-1,
MS-2 = Monosulfate-2

Non-Competitive Slurry Experiments

In addition to the solvent recrystallization experiments, non-competitive slurry experiments were perfoined to search for new solid state forms. These experiments rely on solubility differences of different polymorphic forms (if the compound is polymorphic). As such, only polymorphs having a lower solubility (more stable) than the original crystalline form can result from a noncompetitive slurry experiment. Essentially, when a solid is mixed with solvent as slurry, a saturated solution eventually results. The solution is saturated with respect to the polymorphic form dissolved. However, the solution is supersaturated with respect to any polymorphic form that is more stable (more stable forms have lower solubility) than the polymorphic form initially dissolved. Therefore, any of the more stable polymorphic forms can nucleate and precipitate from solution. In addition, noncompetitive slurry experiments are often useful in identifying solvents that form solvates with the compound.

The slurry experiments were performed by exposing excess "starting" material (Form A) to neat (single) and binary solvent mixtures and agitating the resulting suspensions for several days at ambient temperature. The solids were vacuum filtered and analyzed by XRD to determine the resulting form. To avoid possible desolvation or physical change after isolation, the samples were not further dried before X-ray analysis. A summary of non-competitive slurry experiments is shown in Table 13, below.

TABLE 13

Non-competitive Slurry Experiments

| Vehicle | Initial Form | Duration (days) | Final Form |
|---|---|---|---|
| DMA | A | 27 | monosulfate |
| water | A | n/a | all dissolved |
| 2-propanol | A | 27 | A |
| acetonitrile | A | 27 | A |
| acetone | A | 27 | A |
| dichloromethane | A | 27 | A |
| EtOAc | A | 28 | A |
| 2-butanol | A | 28 | A |
| notromethane | A | 28 | A |
| THF | A | 28 | A |
| DMF/acetone (2/1) | A | 19 | monosulfate |
| DMF/acetone (1/1) | A | 19 | monosulfate |
| DMF/acetone (1/2) | A | 19 | monosulfate |
| DMF/heptane (2/1) | A | 19 | monosulfate |
| DMF/heptane (1/1) | A | 19 | monosulfate |
| DMF/heptane (1/2) | A | 19 | monosulfate |
| DMF/2-propanol (2/1) | A | 19 | monosulfate |

TABLE 13-continued

Non-competitive Slurry Experiments

| Vehicle | Initial Form | Duration (days) | Final Form |
|---|---|---|---|
| DMF/2-propanol (1/1) | A | 19 | monosulfate |
| DMF/2-propanol (1/2) | A | 19 | monosulfate |

In general, the XRD patterns of the disulfate changed in about ten of the slurry experiments, as shown in Table 13.

The water slurry experiment was not continued as the material was completely dissolved.

The XRD patterns of the samples from DMA and binary mixtures of DMF with acetone, heptane and/or 2-propanol slurries after 19 to 27 days were similar to one another and different from starting material. All these samples were confirmed as mono sulfate salts by ion chromatography (IC). All the remaining slurry experiments resulted in no significant change to the starting polymorphic form (Form A) based on the x-ray scattering behavior after 27-28 days of treatment.

X-Ray Analysis of Screening Samples

Solids generated from the seven recrystallization panels and from other means (slurry, hydration, annealing, etc.) were analyzed by powder XRD. To mitigate preferred grain effects, a two dimensional detection system was used to collect all the XRD screening data. The two dimensional detector integrates along the concentric Debye cones which helps reduce pattern variation. If bright spots appear in the conical rings, it indicates strong preferred grain effects which can lead to considerable variability in the observed diffraction patterns. Although some disulfate samples tended to exhibit mild preferred grain effects, overall the disulfate did not appear to suffer from severe preferred grain effects. This resulted in XRD data that had low variability for samples of a given polymorphic form.

The XRD data collected using the two dimensional detector was evaluated using a full profile chemometric treatment to determine if the crystalline form of the samples had changed upon recrystallization. The results of this analysis revealed the material appeared to exist in three different groups. These were eventually determined as Form A (starting material) and apparent two polymorphs of mono-sulfate salt.

The original disulfate starting material was designated as Form A. The resulting form designation for each individual (solvent-based) recrystallization experiment is shown in Tables 6 through 12, above.

After establishing a framework of different polymorphic forms, the characteristics of each form were investigated to understand the different solid state forms.

Characterization of Forms/Salts

After classifying the recrystallization data into different forms based on diffraction behavior, each new pattern was studied to determine if other properties of the forms could be differentiated. The characterization of each form began by comparing the diffraction data representative of each form with that from the other forms. This was generally followed by DSC analysis, TGA analysis, Raman spectroscopy, FTIR analysis, and NMR analysis. Sulfate analysis was also done on new pattern samples as the material had a tendency to lose sulfate content upon processing. Table 14 below summarizes the different XRD patterns observed during the study. A discussion of each form follows.

TABLE 14

Summary of Different Crystalline Forms

| Form Designation | Salt Form | Description | Comments |
|---|---|---|---|
| Form A | disulfate | thermo-dynamic polymorph | Good crystallinity. Easy to obtain from solvent recrystallization. Forms hydrate at ≥60% RH. |
| Monosulfate-1 | monosulfate | polymorph | apparent form of monosalt |
| Moniosulfate-2 | monosulfate | polymorph | apparent form of monosalt |

Disulfate Form A

The characteristic diffraction and thermal behavior of this form are shown in FIGS. 1, 2A and 2B, respectively. The diffraction characteristics of this fowl are unique and different from all the other XRD scattering groups. The starting disulfate was designated as Form A.

The XRD patterns representative of Form A samples indicate that the samples were all crystalline and were very similar. The DSC thermogram of this form (Form A) shows a melting endotherm at ~216° C., followed by decomposition. The TGA thermogram shows Form A has less than 0.4% weight loss at 150° C., suggesting the material is dry.

FIGS. 2A and 2B show the DSC and TGA thermograms. The water content of Form A was measured by Karl Fischer and determined to be 0.3 wt %.

Figure 3A:
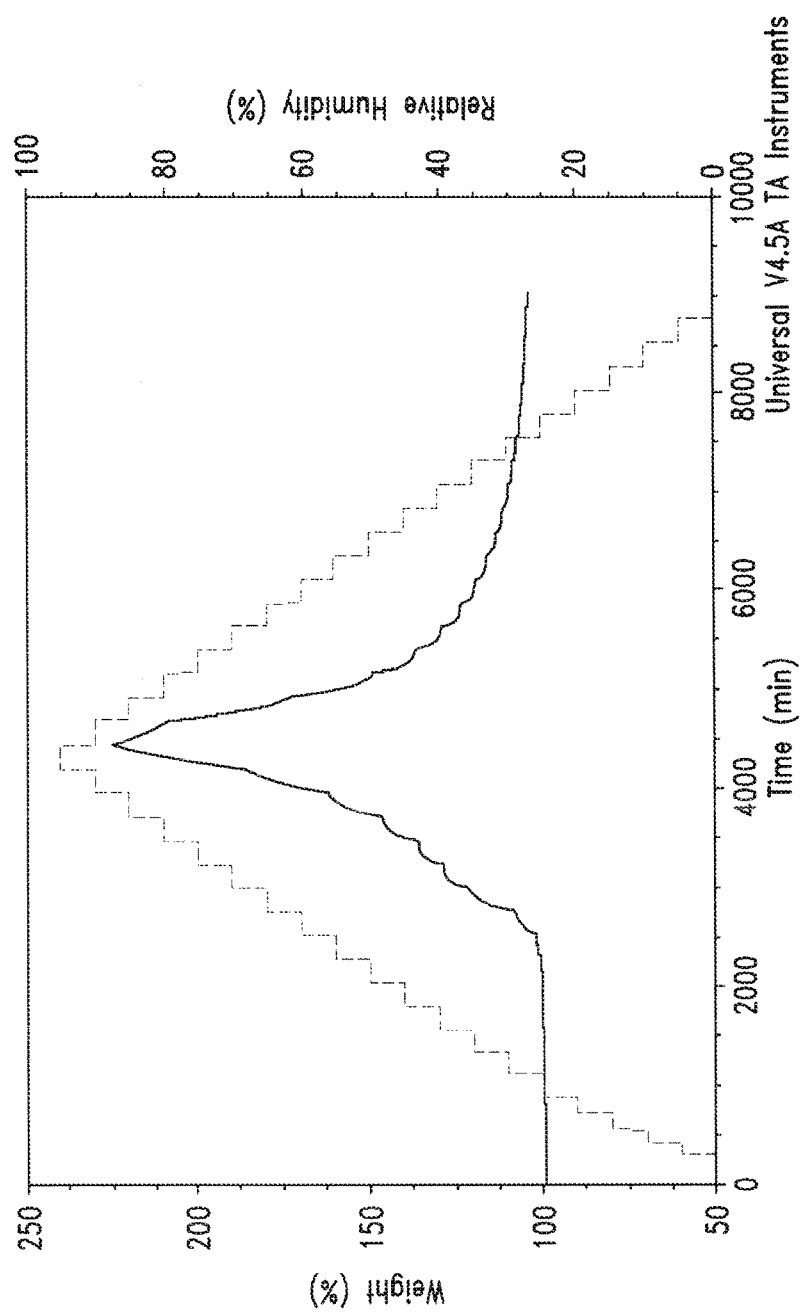
FIG. 3A is a dynamic vapor sorption (DVS) kinetic plot of the crystalline disulfate salt of 2-amino-3-methyl-N-(2-morpholinoethyl)-pentanamide.
Figure 3B:
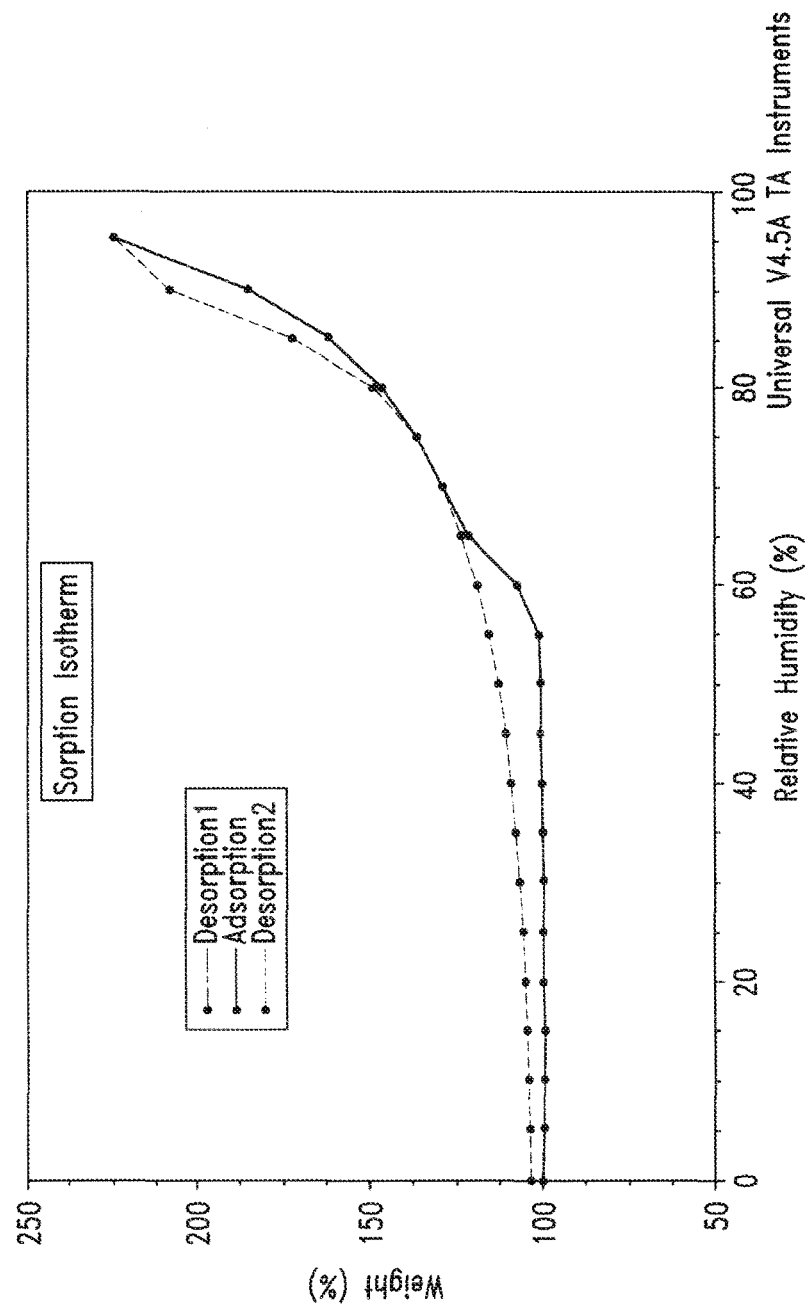
FIG. 3B is a DVS isotherm plot of the crystalline disulfate salt of 2-amino-3-methyl-N-(2-morpholinoethyl)-pentanamide.

FIGS. 3A and 3B show the moisture sorption-desorption isotherm and the kinetic plots for Form A. This sample may undergo hydrate formation ≥60% RH, although the shape of the isotherm is less than ideal. This sample showed an uptake of 2 wt % from 0-55% RH and a total of ~23 wt % at 65% RH followed by a continuous water uptake to the maximum of approximately 225 wt % at 95% RH. During the desorption phase, the sample showed the same behavior of fast loss of weight to ~23 wt % at 65% RH followed by continuous/slow loss to ~4 wt % at the end of the cycle. Apparent deliquescence at high humidity was followed by glass formation upon evaporation.

Solution NMR of Form A is shown in FIG. 4. The spectrum confirms the chemical identity of the material. The solid state FTIR spectrum and Raman spectrum of Form A are shown in FIGS. 5 and 6, respectively. The spectra are consistent with the molecular structure of the disulfate. The amount of sulfate in the Form A by ion chromatography (IC) was determined to be approximately 37 wt %.

Overall, Form A was attributed to a dry polymorphic form of the disulfate, which may form a hydrate when exposed to high humidity at 25° C.

Monosulfate-1

Figure 8B:
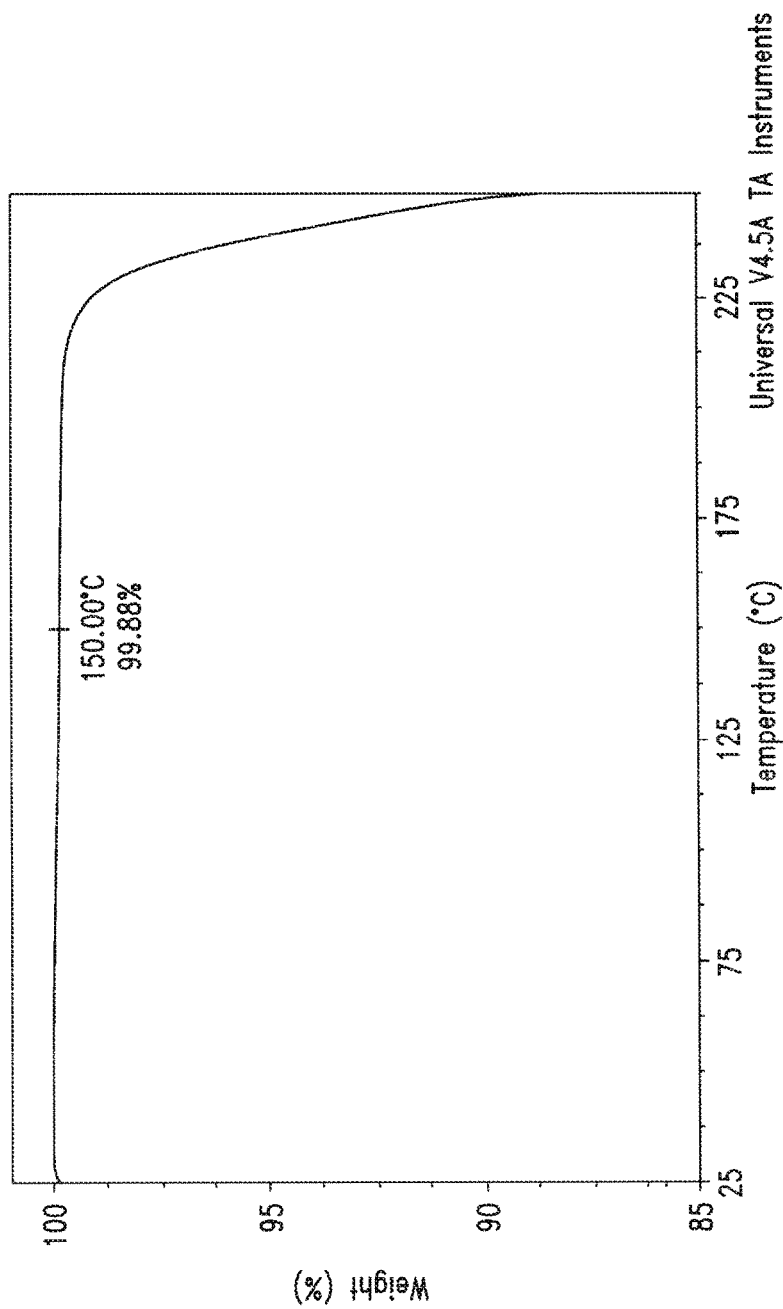
FIG. 8B is a TGA thermogram of a crystalline monosulfate salt (Monosulfate-1) of 2-amino-3-methyl-N-(2-morpholinoethyl)-pentanamide.

The characteristic diffraction and thermal characteristics of this form are shown in FIGS. 7 and 8, respectively. The diffraction characteristics of this are different from the other forms. This form was observed many times in various solvents indicative of the thermodynamic form of the mono-sulfate salt. This form was often observed in the presence of either DMA or DMF. This form was originally thought to be a dry, polymorphic form of 2-amino-3-methyl-N-(2-morpholinoethyl)-pentanamide disulfate. During the characterization, this form was eventually attributed to a dry, polymorphic form of the mono sulfate salt. The XRD patterns of representative samples of Monosulfate-1 indicate it has a reproducible powder pattern and is nicely crystalline. Monosulfate-1 shows approximately 0.3% weight loss at 150° C. by TGA, suggesting a dry material. Figure A8 shows the DSC and TGA thermograms of samples of Monosulfate-1. The DSC thermograms of Monosulfate-1 samples exhibited a broad endotherm with an onset of approximately 245° C. These thermal events were attributed to the melt and decompose behavior of the form.

Figure 9:
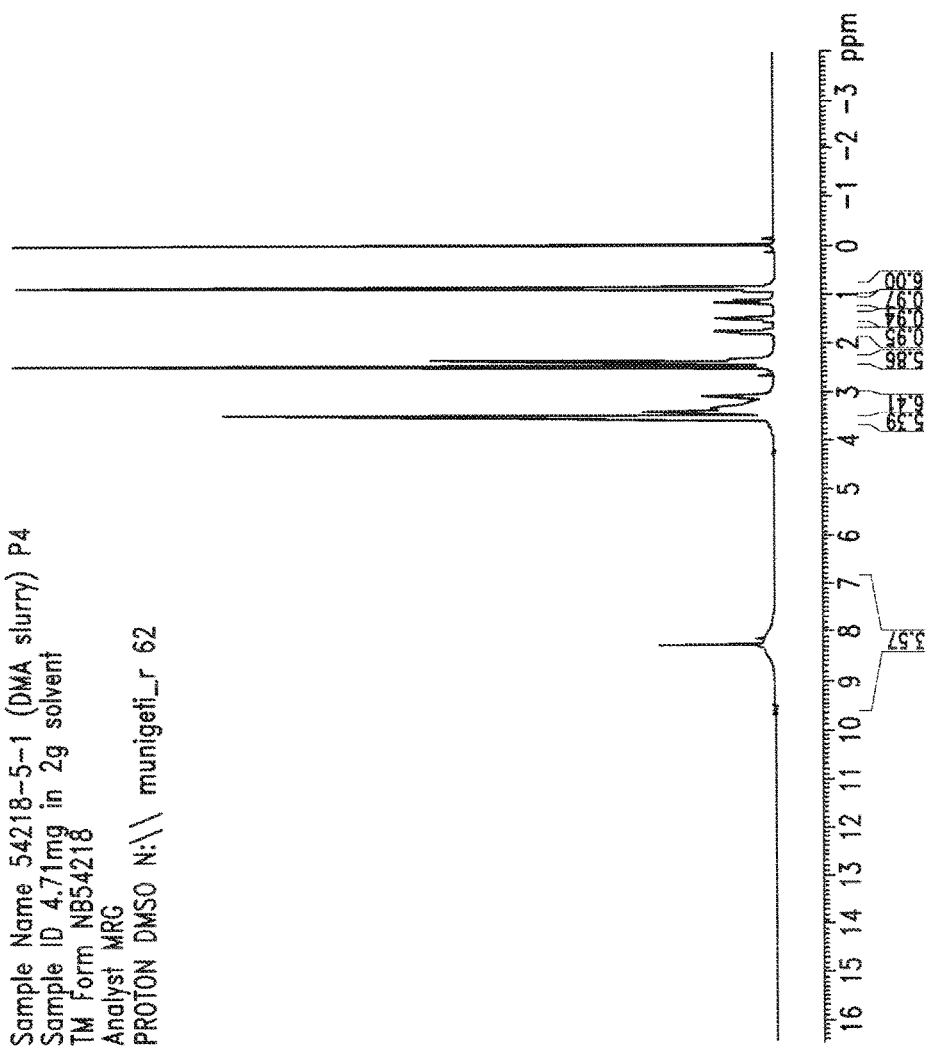
FIG. 9 is a $^1$H-NMR spectrum of a crystalline monosulfate salt (Monosulfate-1) of 2-amino-3-methyl-N-(2-morpholinoethyl)-pentanamide.
Figure 10:
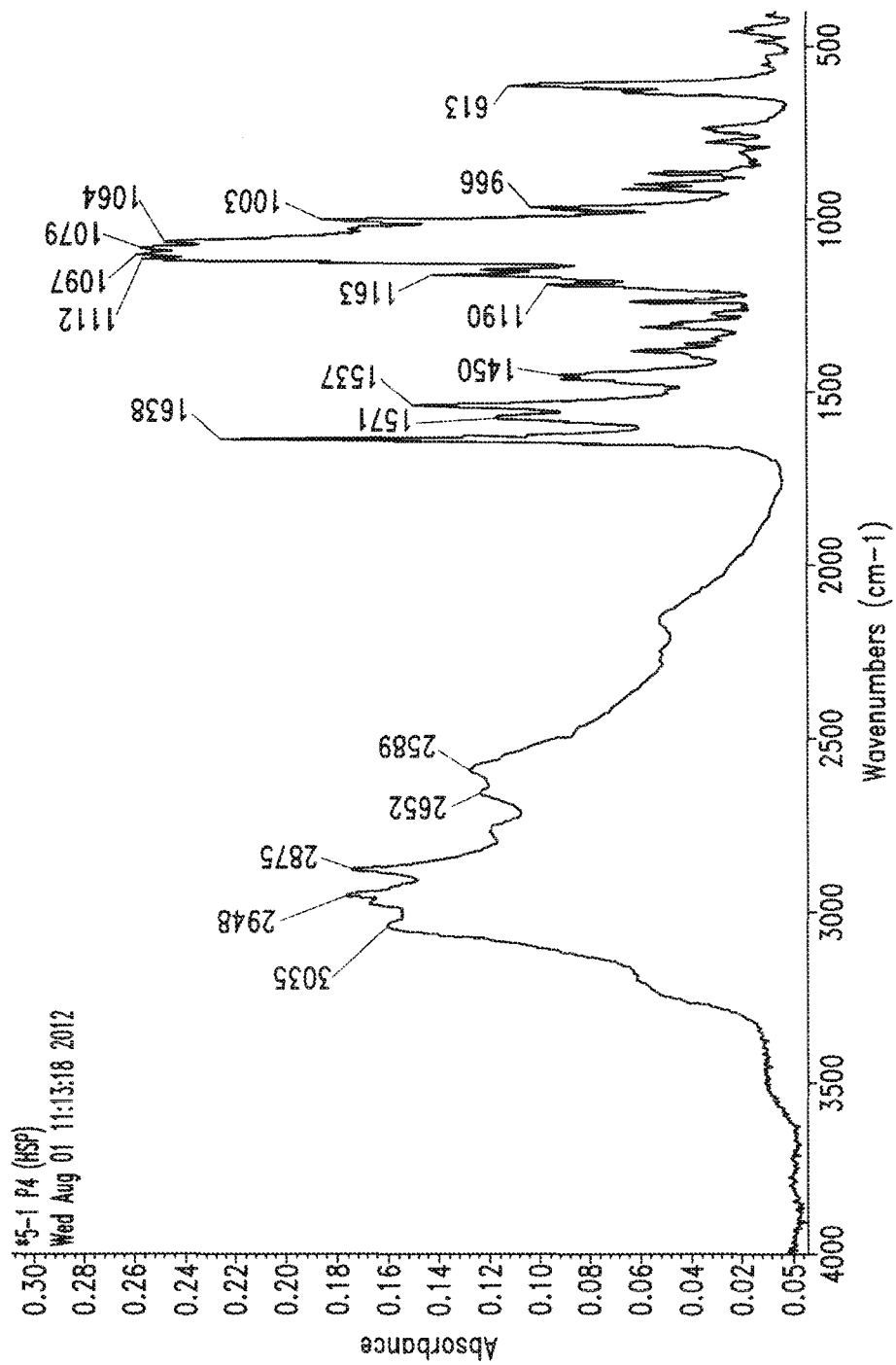
FIG. 10 is a graph of a FT-IR spectrum a crystalline monosulfate salt (Monosulfate-1) of 2-amino-3-methyl-N-(2-morpholinoethyl)-pentanamide.
Figure 11:
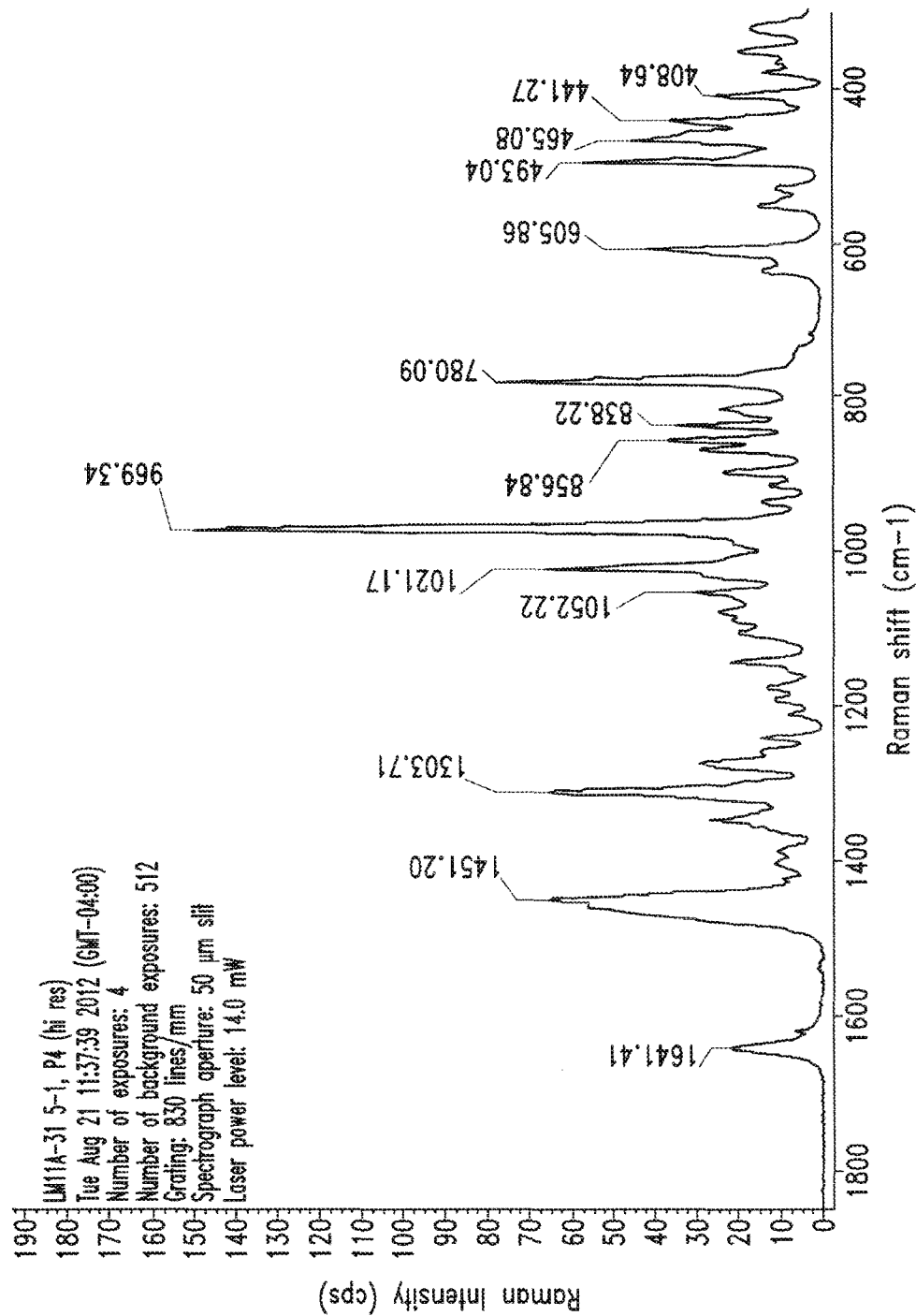
FIG. 11 is a graph of a Raman spectrum a crystalline monosulfate salt (Monosulfate-1) of 2-amino-3-methyl-N-(2-morpholinoethyl)-pentanamide.

The solution NMR spectrum of Monosulfate-1 is shown in FIG. 9. The solid state 1-11R spectrum and Raman spectrum of this Form are shown in FIGS. 10 and 11, respectively. The sulfate analysis by ion chromatography (IC) suggested the representative sample of Monosulfate-1 had 27 wt %, which is identical to the theoretical one mole of sulfate (28 wt %). This suggests that these samples were not the disulfate salt but mono-sulfate salts of 2-amino-3-methyl-N-(2-morpholinoethyl)-pentanamide.

Monosulfate-2

Figure 13:
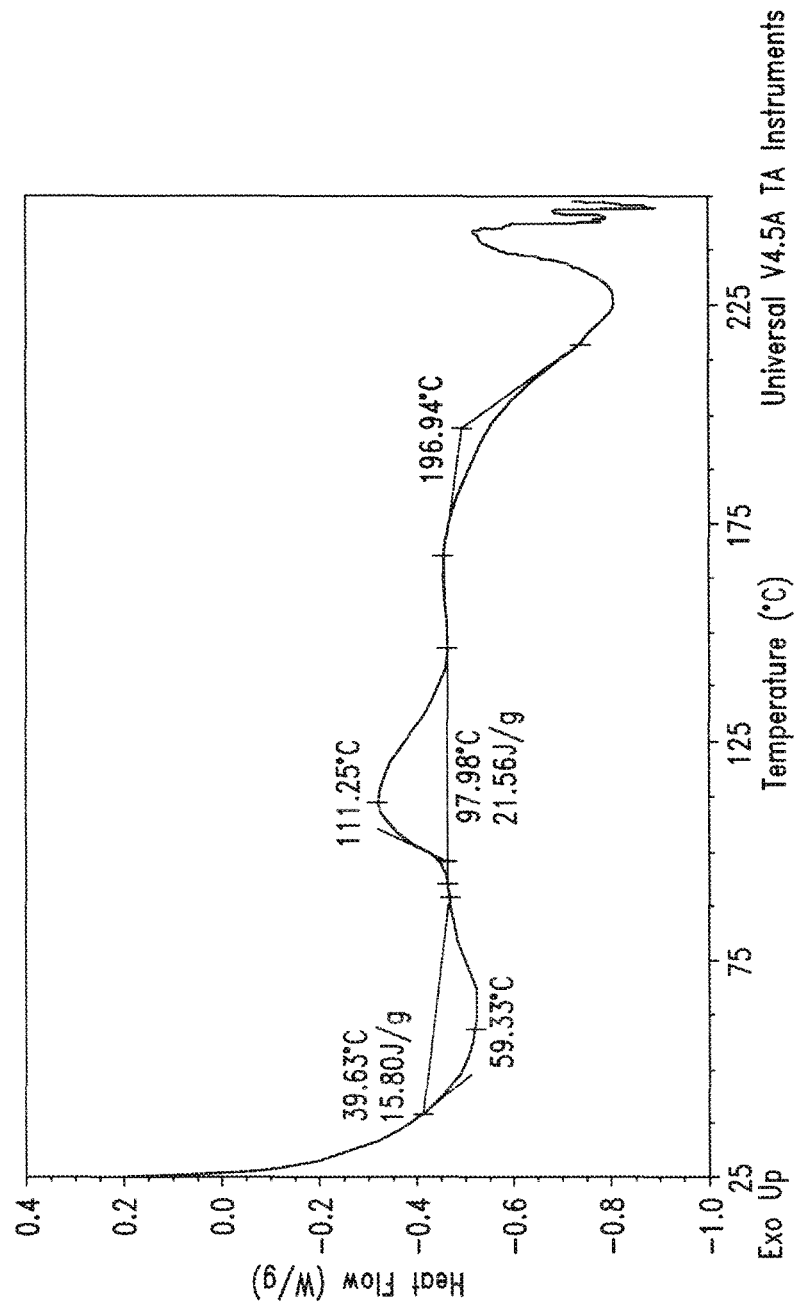
FIG. 13 is a DSC thermogram of a crystalline monosulfate salt (Monosulfate-2) of 2-amino-3-methyl-N-(2-morpholinoethyl)-pentanamide.

The characteristic diffraction and thermal behaviors of this form are shown in FIGS. 12 and 13, respectively. The diffraction characteristics of this form are different than the other samples. This form was observed only two times, from the binary solvent mixtures of either DMF:heptane (1:1) or 2-propanol:chloroform (1:2). These samples had a very low yield due to less solubility of the starting material in any of these solvents.

The XRD pattern of the Monosulfate-2 sample suggested the sample was very low in crystallinity. The DSC thermograms of this sample exhibited a broad endotherm at approximately 40° C. immediately followed by a broad exotherm at ~99° C. followed by a large, broad decomposition endotherm.

Figure 15:
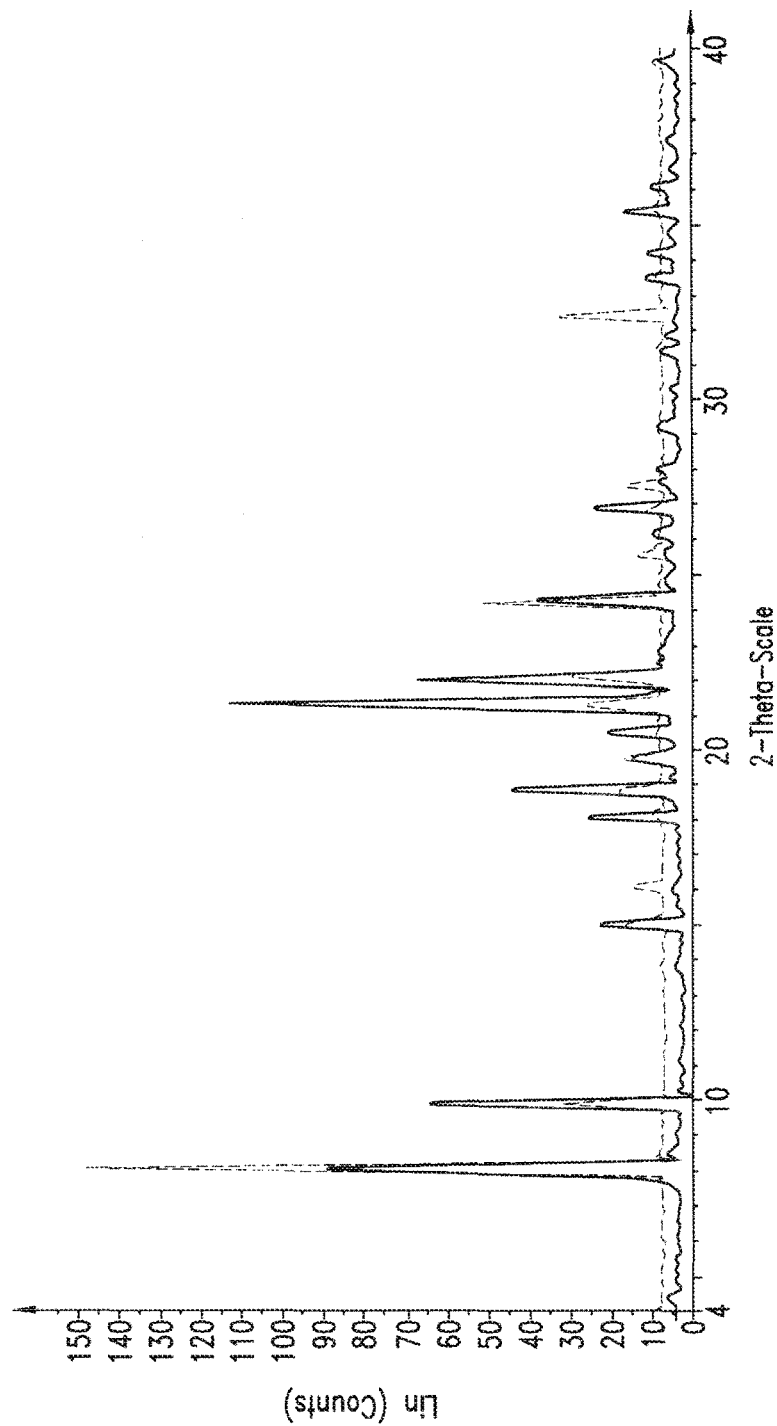
FIG. 15 is an overlay of (i) a XRD pattern of crystalline disulfate salt of 2-amino-3-methyl-N-(2-morpholinoethyl)-pentanamide, and (ii) a XRD pattern of crystalline disulfate salt of 2-amino-3-methyl-N-(2-morpholinoethyl)-pentanamide stored at 43% relative humidity (RH) for about 40 days.
Figure 16A:
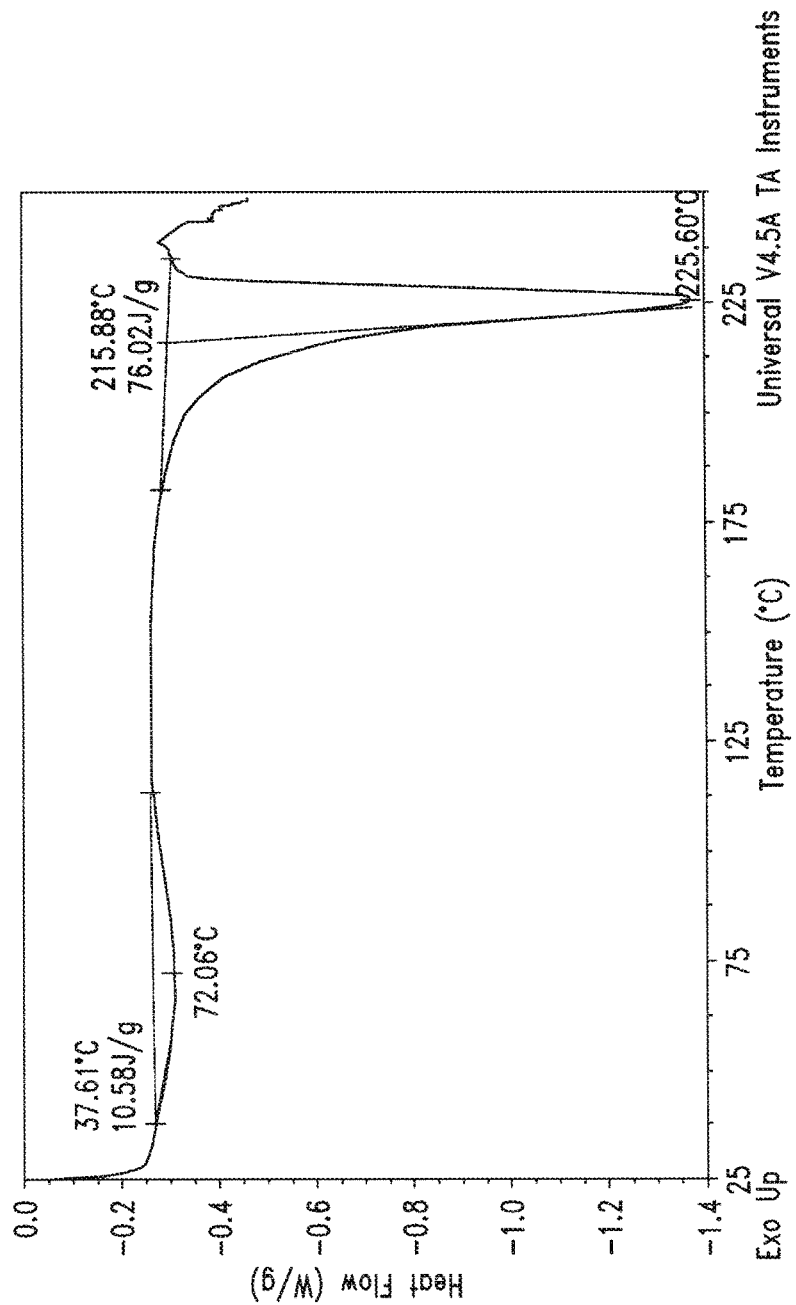
FIG. 16A is a differential scanning calorimetry (DSC) thermogram of the crystalline disulfate salt of 2-amino-3-methyl-N-(2-morpholinoethyl)-pentanamide stored at 43% relative humidity (RH) for about 40 days.
Figure 16B:
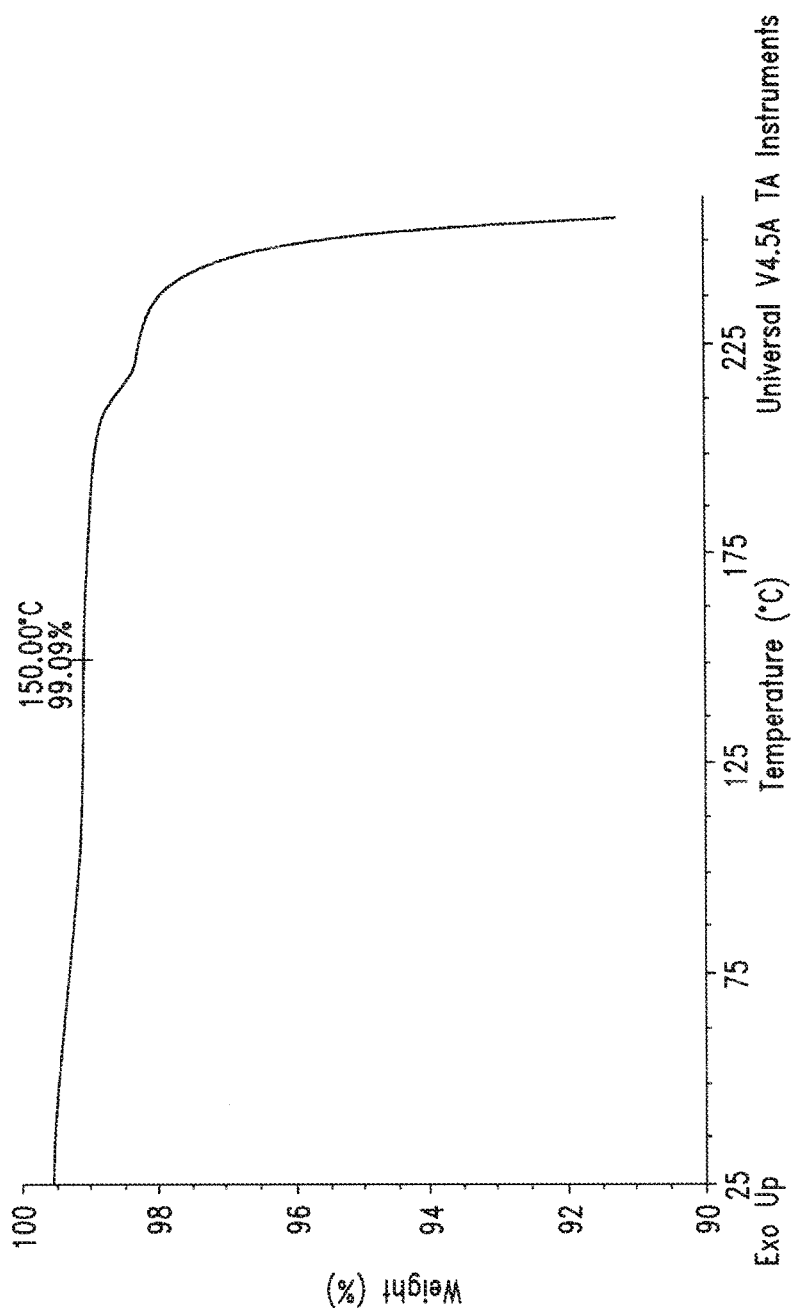
FIG. 16B is a thermogravimetric analysis (TGA) thermogram of the crystalline disulfate salt of 2-amino-3-methyl-N-(2-morpholinoethyl)-pentanamide stored at 43% RH for about 40 days.
Figure 17:
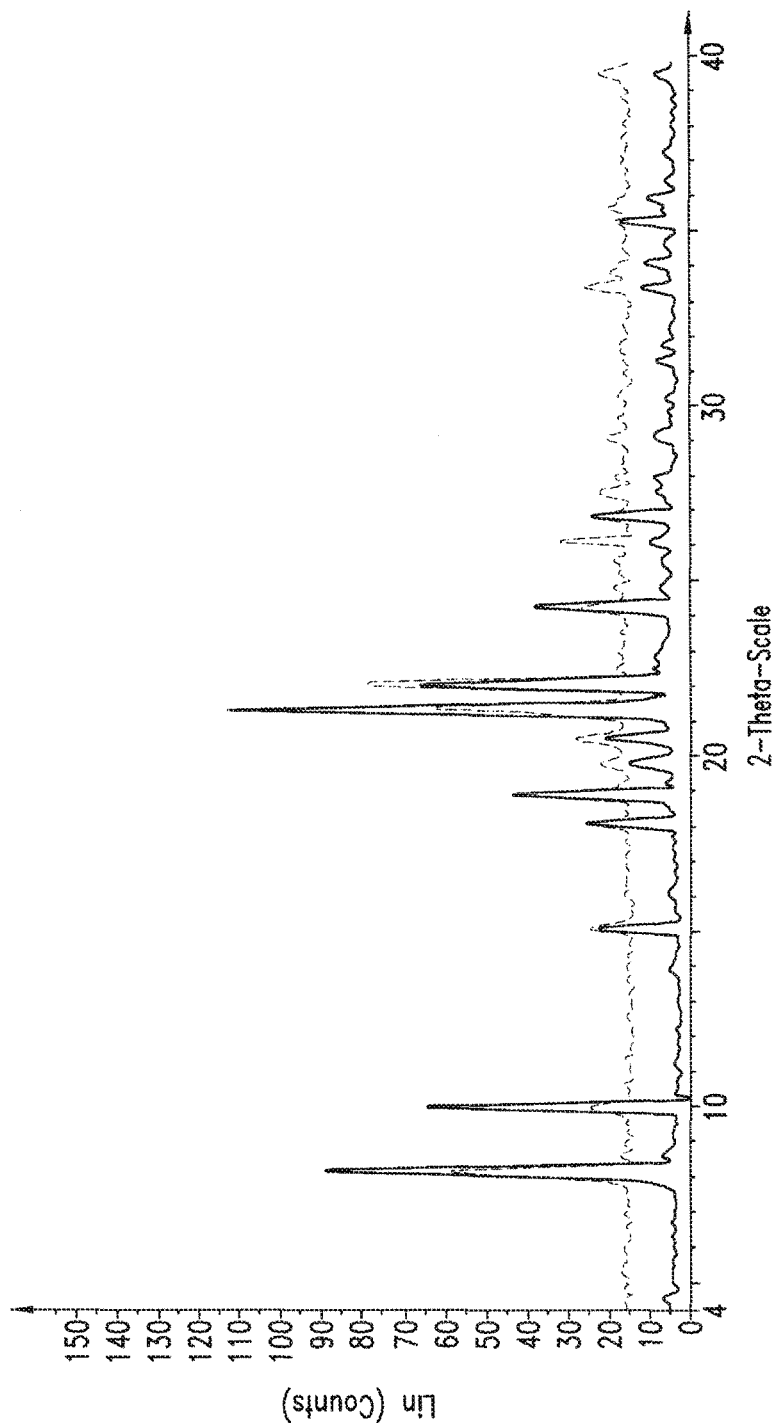
FIG. 17 is an overlay of (i) a XRD pattern of crystalline disulfate salt of 2-amino-3-methyl-N-(2-morpholinoethyl)-pentanamide, and (ii) a XRD pattern of crystalline disulfate salt of 2-amino-3-methyl-N-(2-morpholinoethyl)-pentanamide stored at 53% relative humidity (RH) for about 40 days.
Figure 18A:
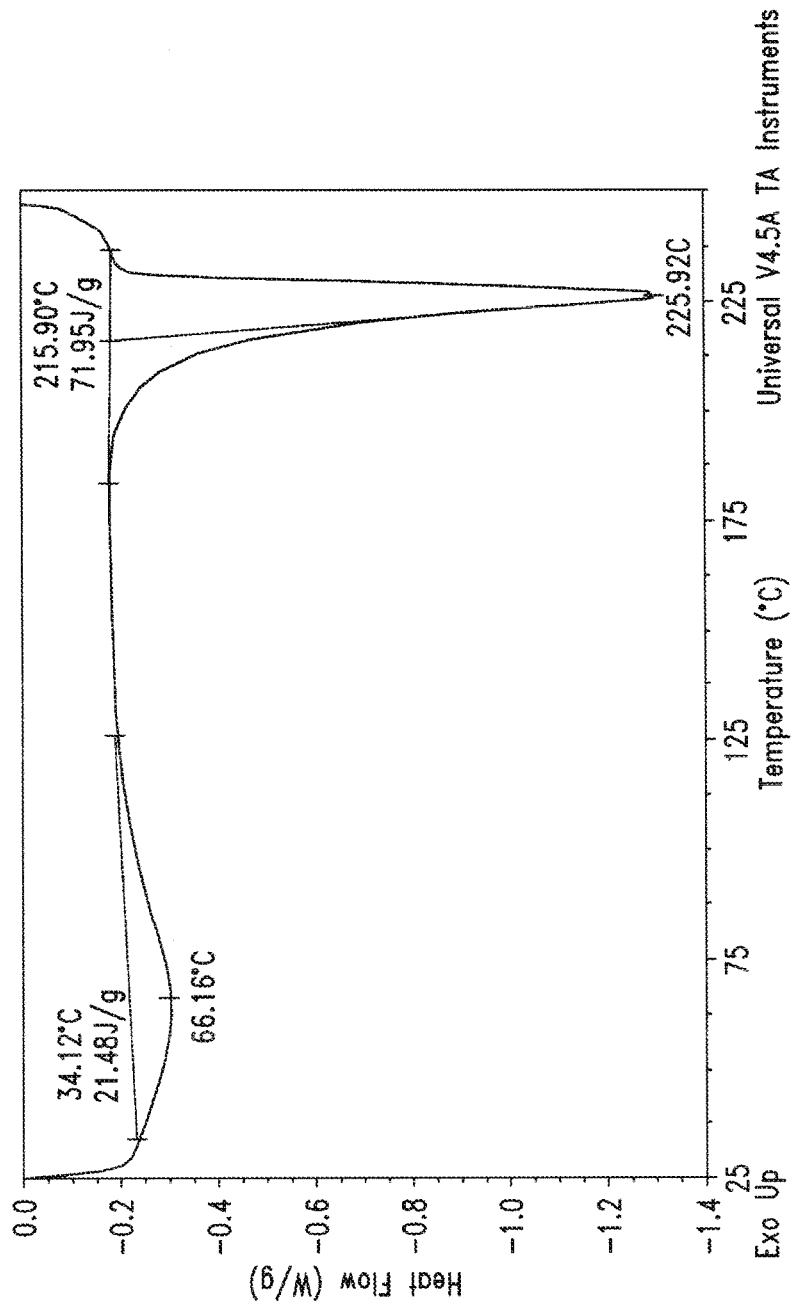
FIG. 18A is a differential scanning calorimetry (DSC) thermogram of the crystalline disulfate salt of 2-amino-3-methyl-N-(2-morpholinoethyl)-pentanamide stored at 43% relative humidity (RH) for about 40 days.
Figure 18B:
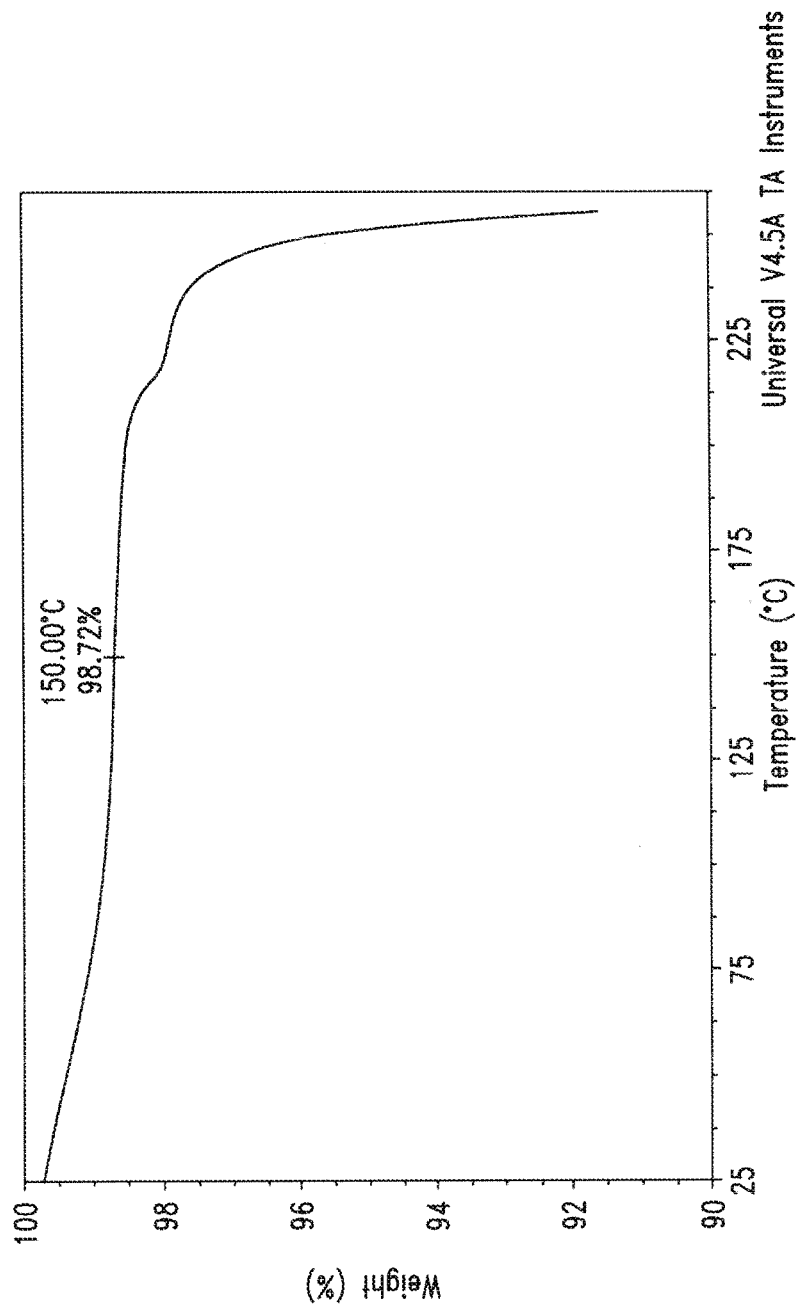
FIG. 18B is a thermogravimetric analysis (TGA) thermogram of the crystalline disulfate salt of 2-amino-3-methyl-N-(2-morpholinoethyl)-pentanamide stored at 43% RH for about 40 days.
Figure 19:
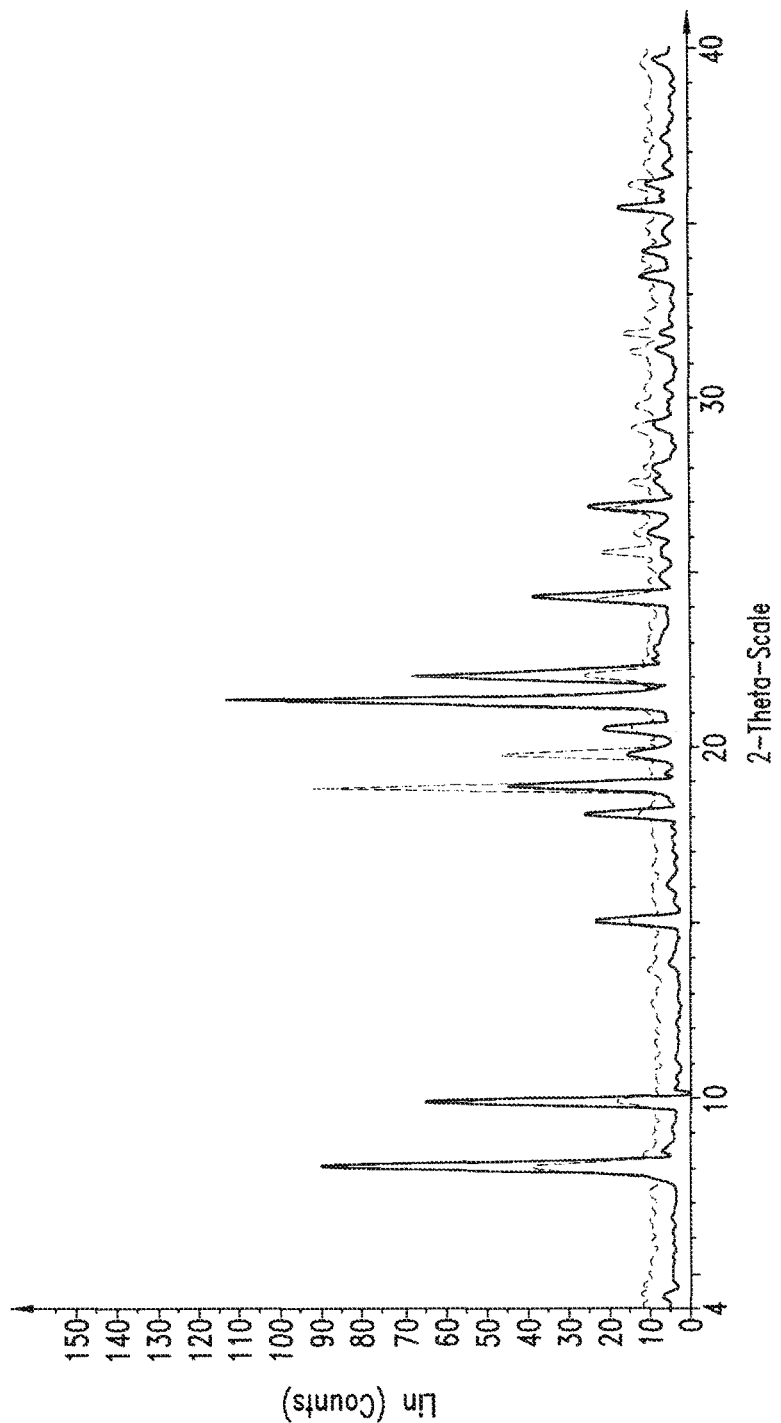
FIG. 19 is an overlay of (i) a XRD pattern of crystalline disulfate salt of 2-amino-3-methyl-N-(2-morpholinoethyl)-pentanamide and (ii) a XRD pattern of crystalline disulfate salt of 2-amino-3-methyl-N-(2-morpholinoethyl)-pentanamide stored at 60% relative humidity (RH) for about 40 days then vacuum dried at 45° C. for 15 days.
Figure 20A:
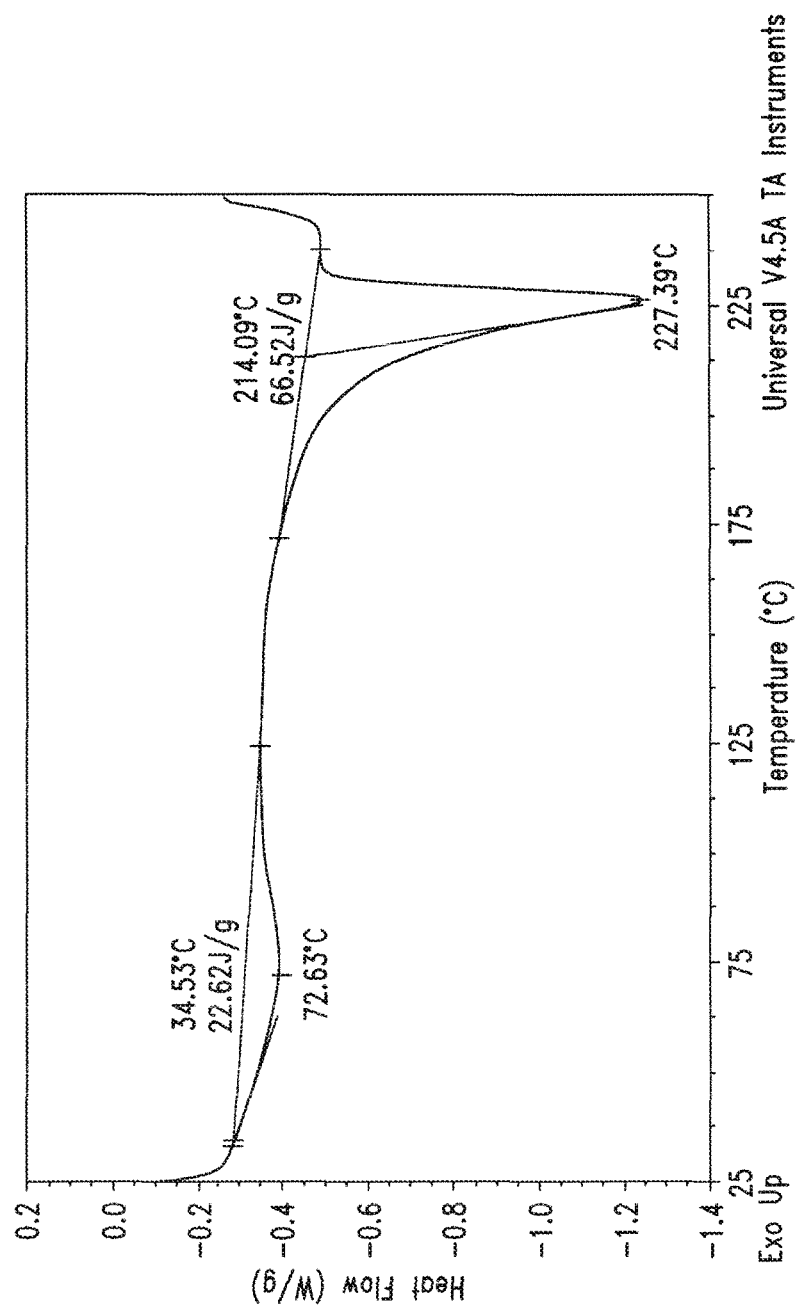
FIG. 20A is a differential scanning calorimetry (DSC) thermogram of the crystalline disulfate salt of 2-amino-3-methyl-N-(2-morpholinoethyl)-pentanamide stored at 60% relative humidity (RH) for about 40 days then vacuum dried at 45° C. for 15 days.
Figure 20B:
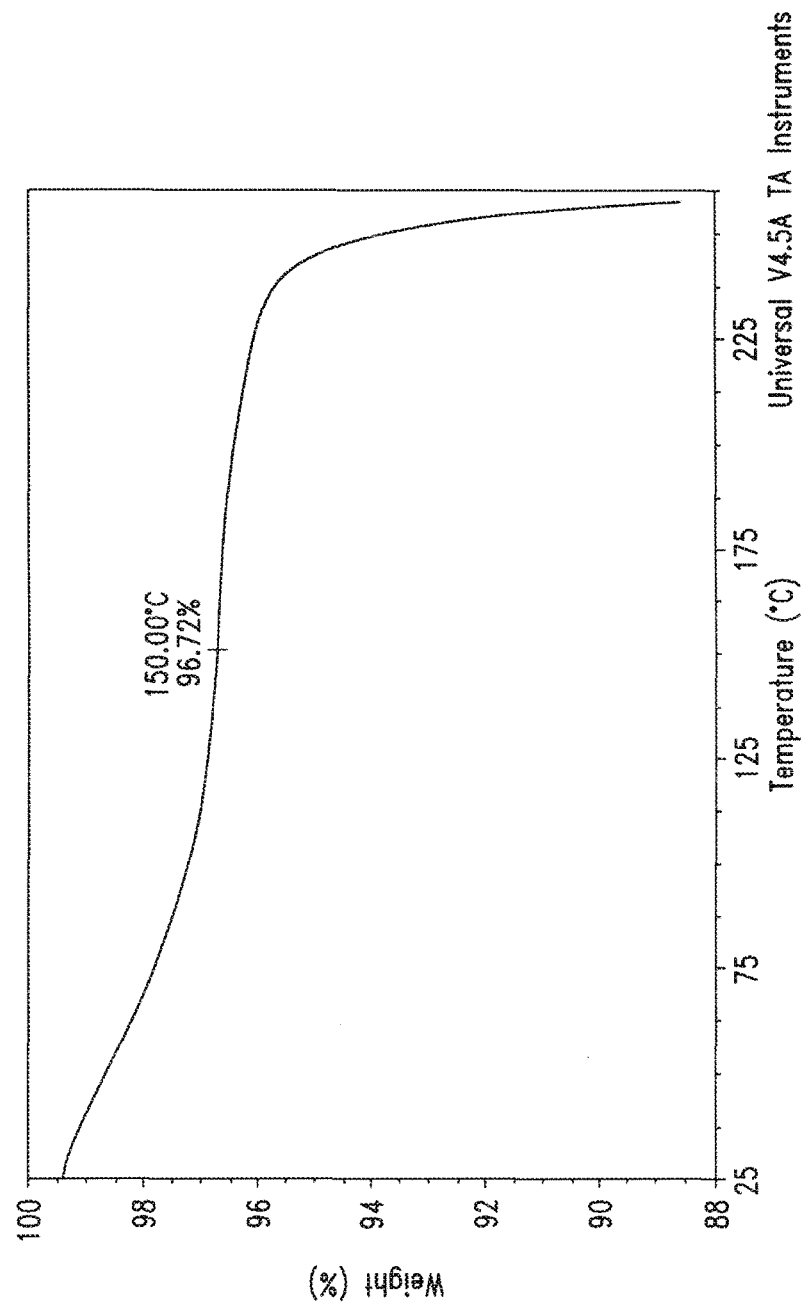
FIG. 20B is a thermogravimetric analysis (TGA) thermogram of the crystalline disulfate salt of 2-amino-3-methyl-N-(2-morpholinoethyl)-pentanamide stored at 60% relative humidity (RH) for about 40 days then vacuum dried at 45° C. for 15 days.

The solution NMR spectrum of Monosulfate-2 is shown in Figure A14. The spectrum is similar to Monosulfate-1, suggesting the material is not a disalt. The solid state FTIR spectrum of Monosulfate-2 is shown in FIG. 15. The spectrum is consistent with the molecular structure of the starting material.

Static Vapor Sorption Studies

Static vapor sorption studies were done in hermetic humidity chambers using saturated salts, or environmental humidity chambers to control the temperature and humidity. Data collected during dynamic vapor sorption studies often are not at theiniodynamic equilibrium. To gain a better understanding of the water uptake and the critical humidity level of the API, samples of the starting material (Form A) were monitored in static humidity chambers to allow the sample to equilibrate with aerial moisture.

In these studies, water vapor sorption was determined gravimetrically (or by Thermogravimetric analysis) by storing samples in open aluminum dishes. Samples were stored at 8 different humidities (23, 33, 43, 53, 60, 69, 75 and 84% RH) at ambient temperature. A few hundred milligrams of Form A was staged at each humidity condition.

The samples were examined periodically either by recording the weight change or by monitoring the water content by Karl Fischer or TGA, and/or XRD pattern. The samples stored at humidities lower than 43% RH showed minimaUno weight gain after 15 days. The samples stored at humidities higher than 60% RH deliquesced after 10 days.

The samples stored at 43 and 53% RH showed gains of approximately 1.0 and 1.3 wt %, respectively, by TGA after 40 days. XRD patterns of these two samples are similar to the starting material. The DSC analysis of these two samples had a broad dehydration endotherm at approximately 35° C. and melting endotheinis same as starting material at approximately 215° C. followed by decomposition. The sulfate analysis by IC of the 43% RH sample suggested this is a disulfate salt with 37 wt % sulfate.

The XRD diffractograms overlay with starting material and thermal behaviors of the samples stored at 43 and 53% RH are shown in FIGS. 15 through 18. The sample stored at 60% RH showed a continuous weight gain to approximately 6 wt % in 20 days followed by mostly deliquesced after 27 days. To understand and isolate the monohydrate sample of the starting material (if existed), this sample was dried at ~45° C. under vacuum for about 15 days. The resulting sample showed approximately 3.3 wt % by TGA and the DSC thermogram had a broad dehydration endotherm at about 35° C. followed by a melting endotherm at 215° C. (similar to starting material). The XRD analysis of this sample is also identical to starting material. The sulfate by IC was approximately 37 wt %, suggesting this is disalt. The XRD overlay with starting material and the thermal behavior of this sample are shown in Figures A19 and A20, respectively.

Figure 21:
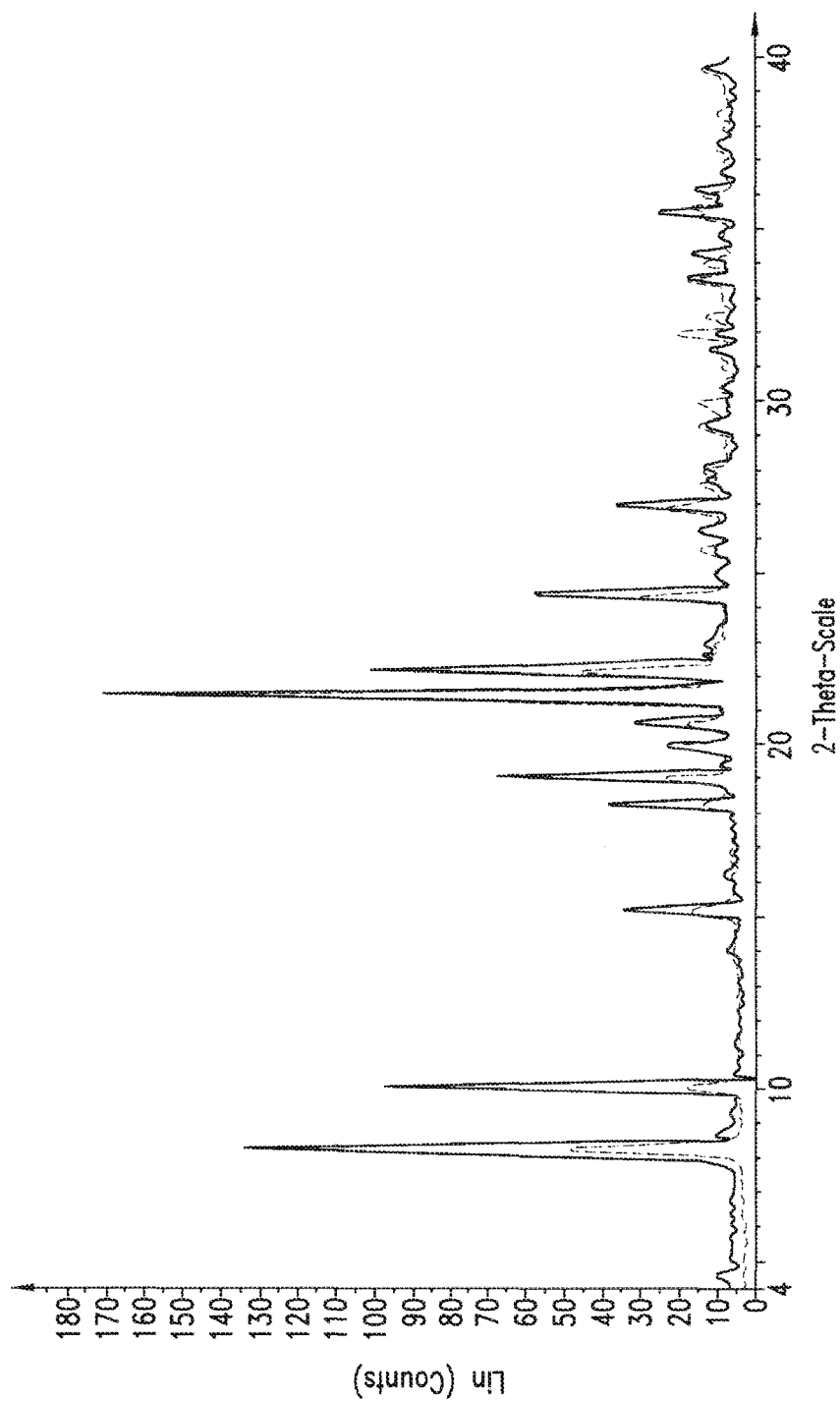
FIG. 21 is an overlay of (i) a XRD pattern of crystalline disulfate salt of 2-amino-3-methyl-N-(2-morpholinoethyl)-pentanamide, and (ii) a XRD pattern of crystalline disulfate salt of 2-amino-3-methyl-N-(2-morpholinoethyl)-pentanamide stored at 60% relative humidity (RH) for about 3 hours.

To understand this further a fresh sample of starting material was staged at 60% RH in DVS for about 3 hours allowing sample to gain about 4 wt %. This sample was then analyzed by XRD and this pattern was similar to the starting material, as shown in. FIG. 21.

Summary

A number of different crystallization conditions were used to produce samples during the course of the study. Form A was seen from many solvents, often an indication of the most stable form. Two new patterns were produced from few binary solvent mixtures and/or DMA slurry, identified as mono-sulfate salts. Form A was the only polymorph of the disulfate salt observed.

Conclusions

The raw diffraction data generated from the polymorph screening experiments (solvent recrystallization, annealing, non-competitive slurries) were categorized into different groups of similar diffraction behavior. Additional experiments were done on these unique crystalline forms (e.g., DSC, TGA, NMR, FTIR, Raman, sulfate analysis, etc.) to refine the forms identified by the diffraction and statistical analysis.

Table 14 summarizes the different crystalline forms of the API discovered when the disulfate form of the drug substance was recrystallized under a large number of conditions. An interesting outcome of the study is the observation that many recrystallization experiments resulted in monosulfate salt.

The DVS analysis suggests the sample has a tendency to foiin hydrates. The study was also complicated somewhat by the difficulty in obtaining hydrate forms. Often the samples stored at 60% RH and above get deliquesced and the samples below would absorb to a max of about 2 wt % and do not observe any difference in solid state pattern. The samples absorbed even 4 wt % moisture does not have any change in XRD pattern.

During the course of the study, three crystalline forms and one amorphous form were observed. Monosulfate-1 and Monosulfate-2 appear to be different anhydrous polymorphs of the mono-sulfate salt form. Although all crystallization experiments started with the disulfate salt form, many experiments resulted in crystalline forms of the mono salt. Samples of recrystallized material resulting in mono salt tend to have approximately 1 mole of sulfate. No solvates of the disulfate salt were discovered during the study.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A crystalline form of (2S,3S)-2-amino-3-methyl-N-(2-morpholinoethyl)-pentanamide monosulfate, wherein the crystalline form exhibits an X-ray powder diffraction pattern comprising peaks at about 23.307±0.3; 15.874±0.3; and 7.896±0.3 degrees two-theta.

2. The crystalline form of claim 1, wherein the X-ray powder diffraction pattern further comprises peaks at about 21.018±0.3 and 9.818±0.3 degrees two-theta.

3. The crystalline form of claim 1, which exhibits an IR spectrum comprising peaks at about 2948±10; 1638±10; and 1097±10 cm$^{-1}$.

4. The crystalline form of claim 3, wherein the IR spectrum further comprises peaks at about 2589±10; 1079±10 and 613±10 cm$^{-1}$.

5. The crystalline form of claim 1, which exhibits a Raman spectrum comprising peaks at about 1451.20±10; 969.34±10; and 780.09±10 cm$^{-1}$.

6. The crystalline form of claim 5, wherein the Raman spectrum further comprises peaks at about 1308.71±10, 1021.17±10 and 493.04±10 cm$^{-1}$.

7. The crystalline form of claim 1, which exhibits a Differential Scanning Calorimetry (DSC) thermogram comprising an endotherm having an onset at about 245±2.0° C.

8. The crystalline form of (2S,3S)-2-amino-3-methyl-N-(2-morpholinoethyl)-pentanamide monosulfate, wherein the crystalline form exhibits an X-ray powder diffraction pattern comprising peaks at about 7.92±0.3; 17.97±0.3; and 23.49±0.3 degrees two-theta.

9. The crystalline form of claim 8, wherein the X-ray powder diffraction pattern further comprises peaks at about 9.83±0.3 and 15.92±0.3 degrees two-theta.

10. The crystalline form of claim 8, which exhibits an IR spectrum comprising peaks at about 2947±10; 1638±10; and 1097±10 cm$^{-1}$.

11. The crystalline form of claim 10, wherein the IR spectrum further comprises peaks at about 3037±10, 1538±10 and 1064±10 cm$^{-1}$.

12. The crystalline form of claim 8, which exhibits a Differential Scanning Calorimetry (DSC) thermogram having an endotherm having an onset at about 40±2.0° C. and an exotherm having an onset at about 99±2.0° C.

13. A composition comprising the crystalline form of claim 1 or 8.

* * * * *